(12) United States Patent
Klein et al.

(10) Patent No.: US 9,896,442 B2
(45) Date of Patent: Feb. 20, 2018

(54) ANTIFUNGAL TREATMENT

(71) Applicant: Wisconsin Alumni Research Foundation, Floor, WI (US)

(72) Inventors: Bruce Steven Klein, Madison, WI (US); Brad Mark Tebbets, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/088,815

(22) Filed: Apr. 1, 2016

(65) Prior Publication Data

US 2016/0289224 A1    Oct. 6, 2016

Related U.S. Application Data

(60) Continuation of application No. 14/029,069, filed on Sep. 17, 2013, now abandoned, which is a division of application No. 13/089,704, filed on Apr. 19, 2011, now abandoned.

(60) Provisional application No. 61/325,548, filed on Apr. 19, 2010.

(51) Int. Cl.

| | |
|---|---|
| *A01N 43/08* | (2006.01) |
| *A61K 31/341* | (2006.01) |
| *C07D 417/12* | (2006.01) |
| *A01N 43/82* | (2006.01) |
| *A61K 31/345* | (2006.01) |
| *A61K 31/4196* | (2006.01) |
| *A61K 31/427* | (2006.01) |
| *A61K 31/433* | (2006.01) |
| *A01N 43/653* | (2006.01) |
| *A01N 43/78* | (2006.01) |
| *C07D 307/66* | (2006.01) |
| *C07D 307/71* | (2006.01) |

(52) U.S. Cl.
CPC ........... *C07D 417/12* (2013.01); *A01N 43/08* (2013.01); *A01N 43/653* (2013.01); *A01N 43/78* (2013.01); *A01N 43/82* (2013.01); *A61K 31/341* (2013.01); *A61K 31/345* (2013.01); *A61K 31/4196* (2013.01); *A61K 31/427* (2013.01); *A61K 31/433* (2013.01); *C07D 307/66* (2013.01); *C07D 307/71* (2013.01)

(58) Field of Classification Search
None
See application file for complete search history.

(56) References Cited

U.S. PATENT DOCUMENTS 3,870,725 A    3/1975 Hughes et al.
5,885,782 A    3/1999 Edwards

OTHER PUBLICATIONS

Fan et. al., Bioorganic & Medicinal Chem. Letters, 1997, 7(24): 3107-3112.*
Baddley, et al., Antifungal Combination Therapy, Clinical Potential, Drugs, 2005, 65(11):1461-1480.
Deschenes, et al., Antifungal Properties and Target Evaluation of Three Putative Bacterial Histidine Kinase Inhibitors, Antimicrobial Agents and Chemotherapy, 1999, 43(7)1700-1703.
Fan, et al., Ester Prodrugs of Ampicillin Tailored for Intracellular Accumulation, Biorganic & Medicinal Chemistry Letters, 1997, 7(24):3107-3112.
Gudlaugsson, et al., Attributable Mortality of Nosocomial Candidemia, Revisited, Clinical Infectious Diseases, 2003, 37:1172-1177.
Hilliard, et al., Multiple Mechanisms of Action for Inhibitors of Histidine Protein Kinases from Bacterial Two-Component Systems, Antimicrobial Agents and Chemotherapy, 1999, 43(7):1693-1699.
Morgan, et al., Incidence of Invasive Aspergillosis Following Hematopoietic Stem Cell and Solid Organ Transplantation: Interim Results of a Prospective Multicenter Surveillance Program, Medical Mycology Supplement 1, 2005, 43:S49-S58.
Motoyama, et al., An Os-1 Family Histidine Kinase from a Filamentous Fungus Confers Fungicide-Sensitivity to Yeast, Curr. Genet., 2005, 47:298-306.
Nett, et al., Optimizing a Candida Biofilm Microtiter Plate Model for Measurement of Antifungal Susceptibility by Tetrazolium Salt Assay, Journal of Clinical Microbiology, 2011, 49(4):1426-1433.
Nosanchuk, Current Status and Future of Antifungal Therapy for Systemic Mycoses, Recent Patents on Anti-Infective Drug Discovery, 2006, 1(1):75-84.
Nucci, et al., Emerging Fungal Diseases, Clinical Infectious Diseases, 2005, 41:521-526.
Sanglard, et al., Resistance of Candida Species to Antifungal Agents: Molecular Mechanisms and Clinical Consequences, The Lancet Infectious Diseases, 2002, 2(2):73-85.
Uppuluri, et al., Synergistic Effect of Calcineurin Inhibitors and Fluconazole Against Candida Albicans Biofilms, Antimicrobial Agents and Chemotherapy, 2008, 52(3):1127-1132.
Wisplinghoff, et al., Nosocomial Bloodstream Infections in US Hospitals: Analysis of 24,179 Cases From a Prospective Nationwide Surveillance Study, Clinical Infectious Diseases, 2004, 39:309-317.
Tebbets, et al., Identification of Novel Small Molecules with Broad-Spectrum Antifungal Activity, Poster, Apr. 2010, 1 page.
Compendium of Pesticide Common Names—Fungicides, http://www.alanwood.net/pesticides/class_fungicides.html, accessed May 16, 2011, 13 pages.
STN Document No. 78:4286, Title: 5-Nitro-2-thiazolylsulfides, Inventors: Hughes, et al., Copyright 2013 ACS on STN, 6 pages.
Presentation at Perlman Symposium, Apr. 23, 2010, 12 pages.

* cited by examiner

*Primary Examiner* — Svetlana M Ivanova
(74) *Attorney, Agent, or Firm* — Quarles & Brady LLP

(57) ABSTRACT

A method of treating or preventing fungal infection, which includes identifying a plant or animal having a fungal infection and administering an effective amount of an antifungal composition to the plant or animal to reduce the fungal infection. In a preferred form of the present invention, the antifungal composition is compound 13 or 33 and is combined with an azole compound, such as fluconazole.

10 Claims, 20 Drawing Sheets

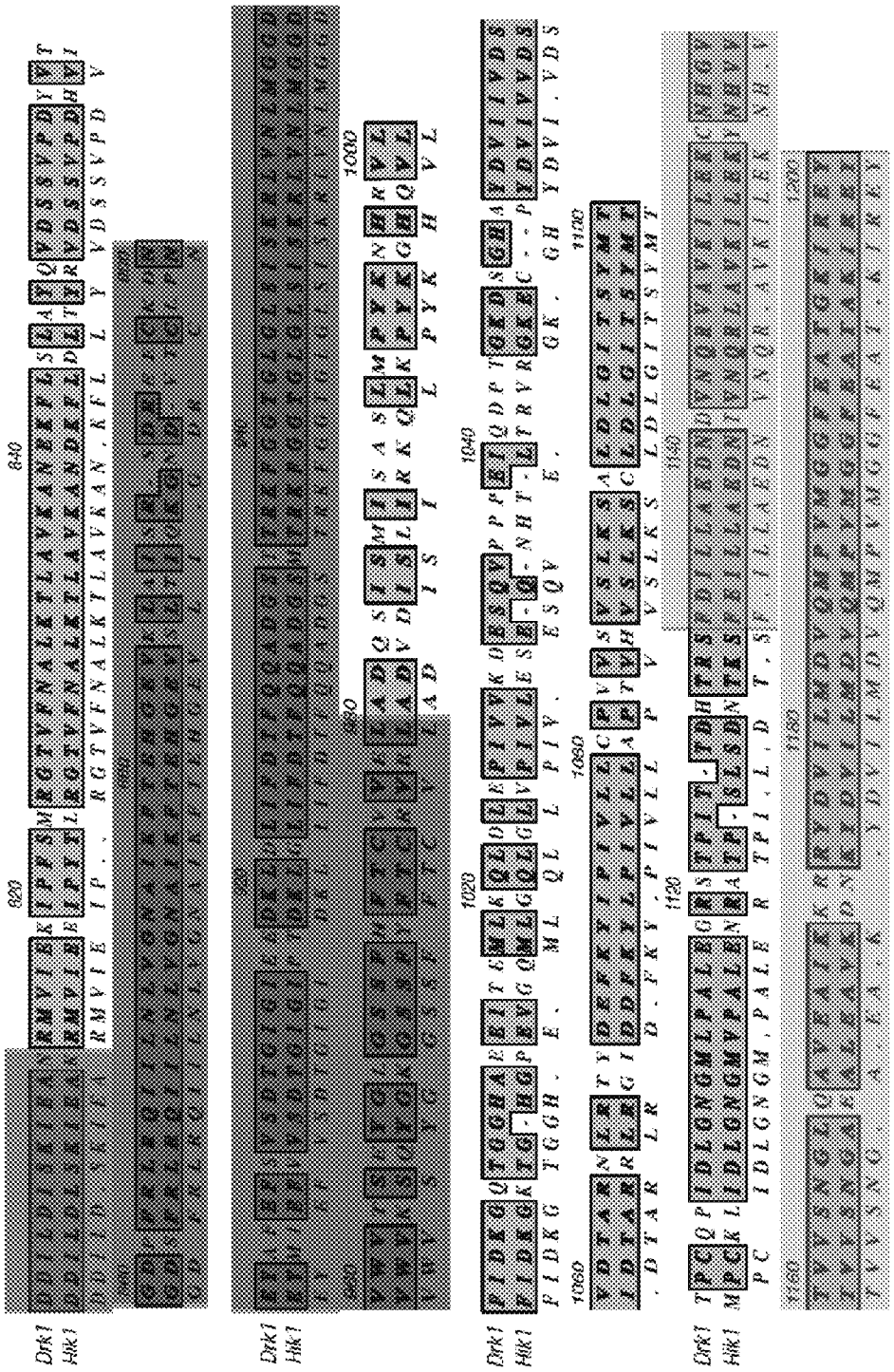
Figure 1 - cont'd

Figure 1 - cont'd

ANTIFUNGAL TREATMENT

CROSS-REFERENCE TO RELATED APPLICATIONS

This is a continuation of U.S. patent application Ser. No. 14/029,069 filed Sep. 17, 2013, which is a division of U.S. patent application Ser. No. 13/089,704 filed Apr. 19, 2011 which claims benefit of U.S. Patent Application 61/325,548 filed Apr. 19, 2010, which are incorporated herein by reference for all purposes.

STATEMENT REGARDING FEDERALLY SPONSORED RESEARCH OR DEVELOPMENT

This invention was made with government support under AI035681 and AI086025 awarded by the National Institutes of Health. The government has certain rights in the invention.

BACKGROUND

The incidence of invasive fungal disease has dramatically increased over the past few decades in parallel with the increase in number of immunocompromised patients (J. D. Noshanchuk. Current Status and Future of Antifungal Therapy for Systemic Mycoses. *Recent Patents on Anti-Infective Drug Discovery*, 2006, 1, 75-84). Patients with increased risk for severe fungal disease include those undergoing administration of broad-spectrum antibiotics, corticosteroids and cytotoxic agents, intravenous catheters, invasive medical procedures, and Human Immunodeficiency Virus (HIV) infection.

Toxicity presents one barrier to effective antifungal therapy. An additional factor limiting the effectiveness of antifungal therapy is resistance. Resistance to antifungal therapeutics can result from expression of efflux pumps which reduce drug accumulation, alteration of target proteins, and modification of membrane sterol composition (Sanglard D, Odds F C. Resistance of *Candida* species to antifungal agents: molecular mechanisms and clinical consequences. Lancet Infect Dis 2002; 2(2): 73-85).

The clinical consequences of antifungal resistance are evident in treatment failures as well as in the changing prevalence of fungi, such as for *Candida* spp. and emerging moulds, causing disease (Baddley J W, Pappas P G. Antifungal combination therapy: clinical potential. Drugs 2005; 65(11): 1461-80, Nucci M, Marr K A. Emerging fungal diseases. Clin Infect Dis 2005; 41(4): 521-6. Epub 2005 Jul. 11). *Candida* spp. are the fourth most common cause of bloodstream infection in the U.S. (Wisplinghoff et al., Nosocomial bloodstream infections in US hospitals: analysis of 24,179 cases from a prospective nationwide surveillance study. Clin Infect Dis 2004; 39(3): 309-317) with an attributable mortality rate of approximately 40% (Gudlaugsson O, Gillespie S, Lee K, et al. Attributable mortality of nosocomial candidemia, revisited. Clin Infect Dis 2003; 37(9): 1172-7. Epub 2003 Oct. 8). Currently, the incidence of aspergillosis in the US ranges from 0.5% after autologous hematopoietic stem cell transplantation to 3.9% after transplantation from an unrelated donor (Morgan J, Wannemuehler K A, Marr K A, et al. Incidence of invasive aspergillosis following hematopoietic stem cell and solid organ transplantation: interim results of a prospective multicenter surveillance program. Med Mycol 2005; 43(Suppl 1): S49-58). In these patients, mortality 3 months after diagnosis of aspergillosis was 53.8% in autologous transplant recipients and 84.6% in those with unrelated donor transplants (Morgan J, Wannemuehler K A, Marr K A, et al. Incidence of invasive aspergillosis following hematopoietic stem cell and solid organ transplantation: interim results of a prospective multicenter surveillance program. Med Mycol 2005; 43(Suppl 1): S49-58).

These data clearly show the need for new approaches to combating systemic mycoses, which could be effective in humans. Moreover, fungus-specific interventions could prove valuable in combating infections in other animals as well as plants.

SUMMARY OF THE INVENTION

In one embodiment, the present invention is a method for treating fungal infection, comprising: (a) identifying a plant or animal having a fungal infection; and (b) administering an effective amount of an anti-fungal compound to the plant or animal, wherein the amount is effective to reduce the fungal infection and wherein the compound comprises formula I or formula IV.

In one embodiment, the compound comprises a compound of formula (I):

wherein $R^1$ is >S (preferably), or oxidized S, for example >SO and >$SO_2$, $R^2$ and $R^3$ are independently selected from formulas (II) and (III):

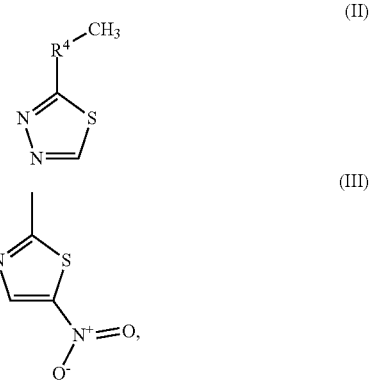

and $R^4$ is >S (preferably), or oxidized S, for example >SO and >$SO_2$, or a salt, prodrug, solvate or hydrate thereof.

In a second embodiment, the compound comprises a compound of formula (IV):

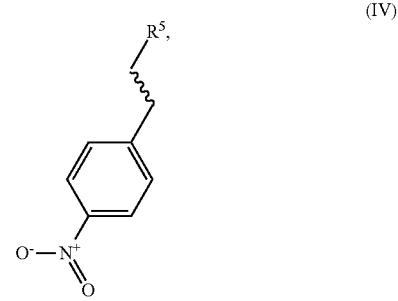

wherein ~~~ is an alkane, alkene, or alkyne (preferably an alkene or an alkyne), and $R^5$ is selected from the group consisting of formulas (V), (VI), (VII), and (VIII):

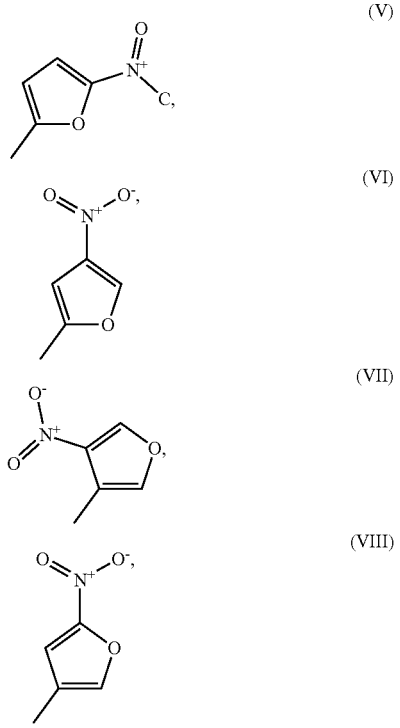

or a salt, prodrug, solvate or hydrate thereof.

Preferably the compound comprises at least one of:

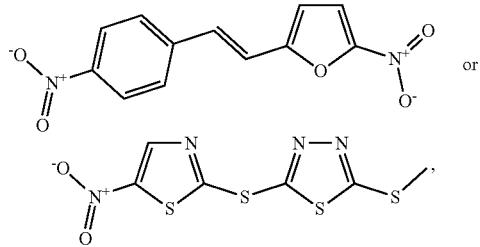

or a salt, prodrug, solvate or hydrate thereof.

In a separate embodiment, the method additionally comprises administering an amount of azole, preferably fluconazole, compound effective to reduce fungal infection.

DESCRIPTION OF THE INVENTION

Figure 1:
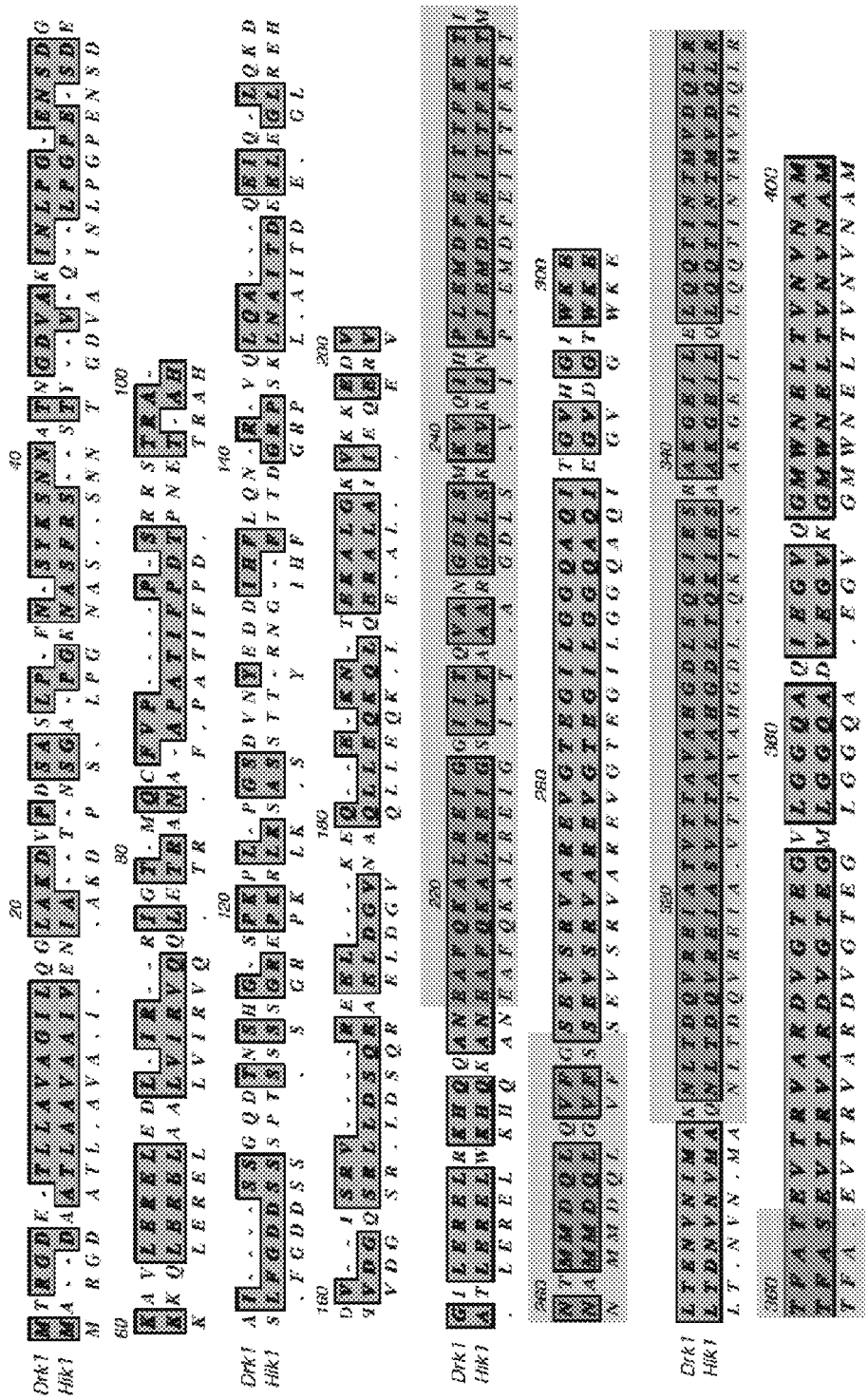
FIG. 1. Protein sequence alignments of Drk1 and Hik1. Drk1 is 78% identical to Hik1. The amino acid motifs of hybrid-histidine kinases are highlighted: HAMP (circles), HisKA (vertical lines), HATPase (horizontal lines), Receiver (black).
Figure 1:
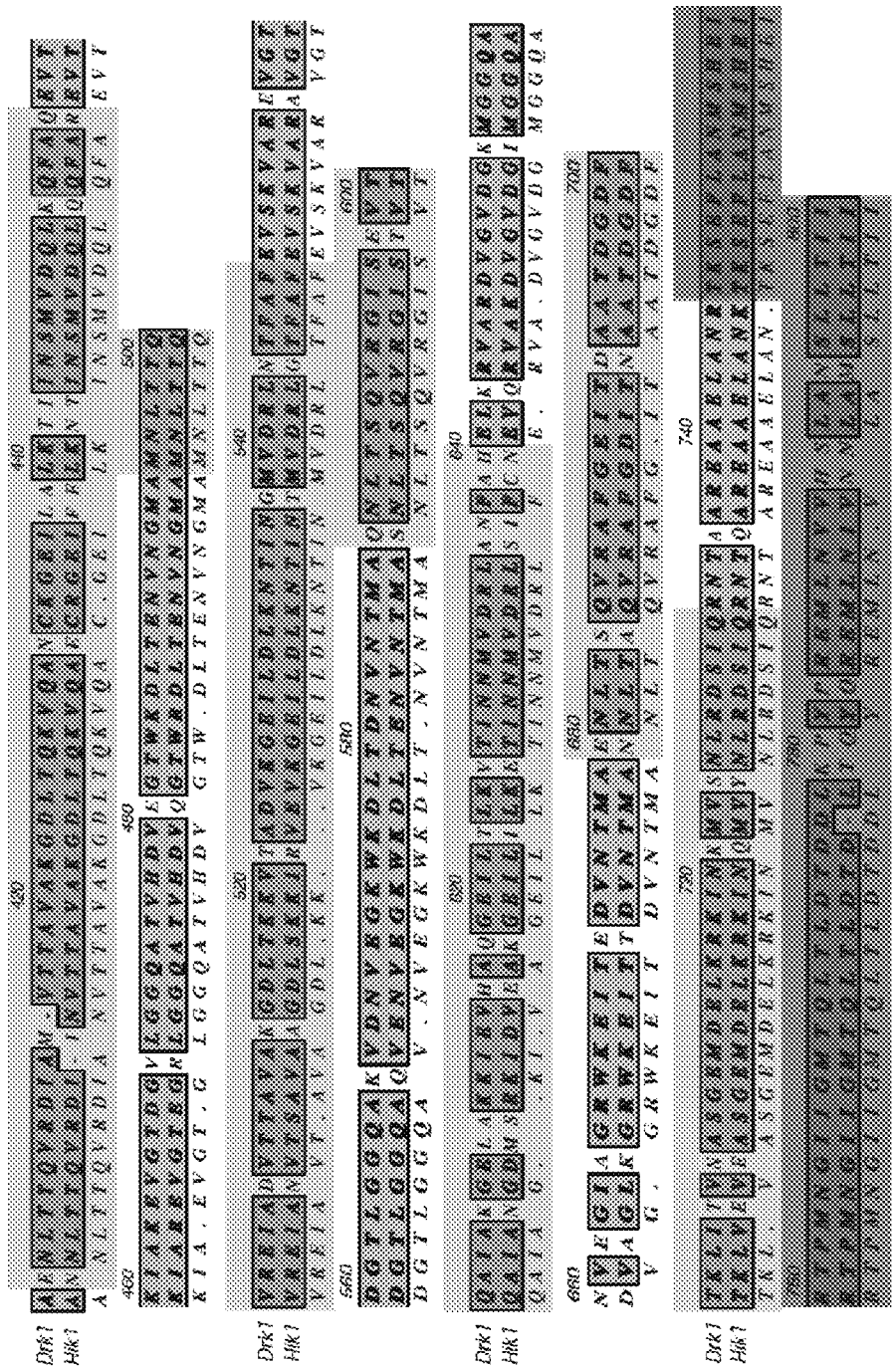
Figure 2:
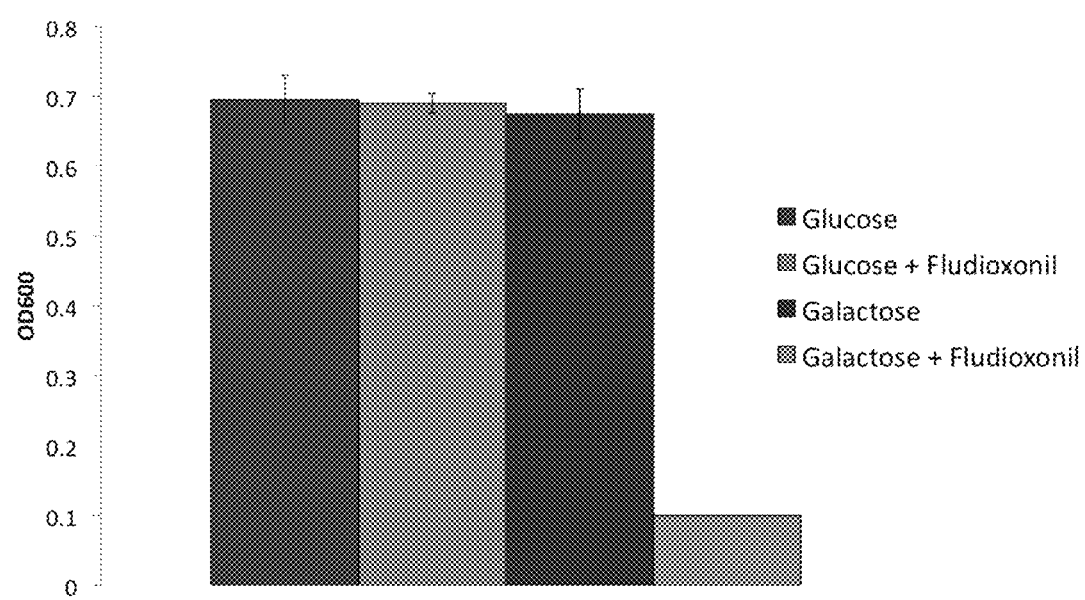
FIG. 2. Expression of Hik1 fludioxonil sensitivity to Saccharomyces. Growth of Hik1 Saccharomyces in glucose, which does not induce Hik1, was uninhibited by fludioxonil. Hik1 Saccharomyces was able to grow on galactose alone, but the addition of fludioxonil inhibited Saccharomyces growth. The experiment was performed in triplicate. Error bars represent the standard deviation.

Histidine kinases regulate fungal stress response and are well conserved in fungi but are not present in humans. Recently, a hybrid histidine kinase called Drk1 (dimorphism regulating kinase) was discovered, which regulates morphogenesis and virulence in fungi. Certain features of Drk1 lend themselves to being drug targets. For example, Drk1 is highly conserved throughout the fungal kingdom (see below, Table 1: Histidine Kinase Homologs of Drk1) and absent from the human genome.

In the Examples below, we describe our identification of compounds that target Drk1 and/or related fungal hybrid histidine kinase-dependent mechanisms (collectively, histidine kinase-dependent anti-fungal compounds). In one embodiment of the present invention, these compounds are used to inhibit growth of or eradicate fungi. This use is particularly valuable in light of the limitations of currently available antifungal compounds. The examples also disclose preferable combinations of compound 13 and 33 with other antifungal compositions. Most preferably, the compounds of the present invention can be combined with an azole compound, such as fluconazole, for a synergistic antifungal effect.

In brief, the present invention includes the use of compounds identified as influencing histidine kinase-dependent pathways, including Drk1-dependent pathways, as antifungal agents, as well as salts, prodrugs, solvates or hydrates thereof.

In a preferred embodiment of the present invention, the antifungal agents are selected from the group consisting of compound 13 and compound 33, which are represented by the following formulas:

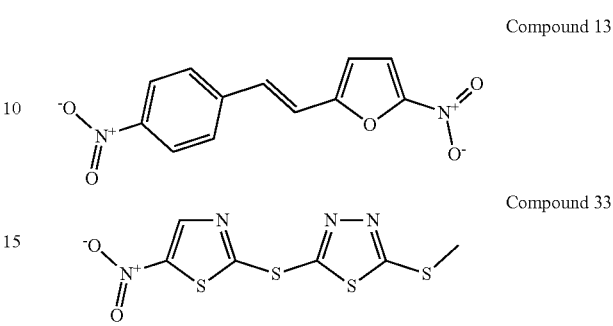

By "compounds of the present invention" we mean to include compound 33 and compound 13, described above, and compounds of identical formula with conservative substitutions. By conservative substitutions, we mean that in compound 13, one may change the substitution pattern on the furan from (2,5) to (3,5), (3,4) or (2,4). One may also change the center double-bond to an alkane or alkyne, although alkynes and alkenes are preferable. In compound 33, we mean that one may oxidize sulfurs that are not part of heterocycles and one may switch the heterocycles or change them both to the same heterocycle.

For example, compounds of the present invention will include:

a compound of formula (I):

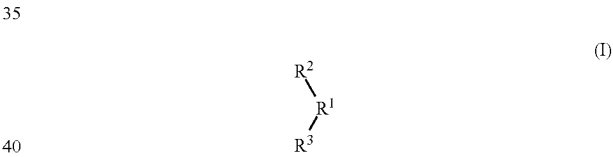

wherein $R^1$ is >S (preferably), or oxidized S, for example >SO and >SO$_2$, $R^2$ and $R^3$ are independently selected from formulas (II) and (III):

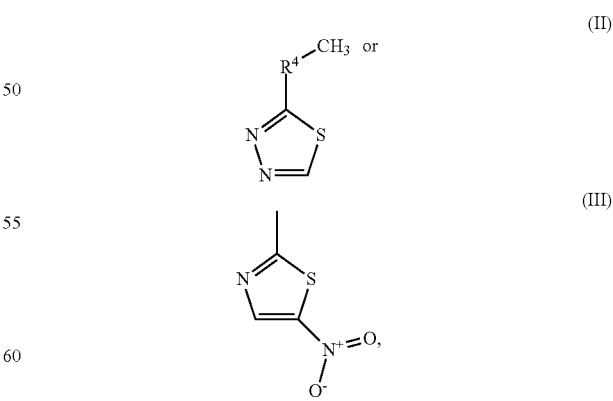

and $R^4$ is >S (preferably), or oxidized S, for example >SO and >SO$_2$, or a salt, prodrug, solvate or hydrate thereof. Formula (I) comprises compound 33 and allows substitutions that do not change the activity of the protein.

Compounds of the present invention will also include: a compound of formula (IV):

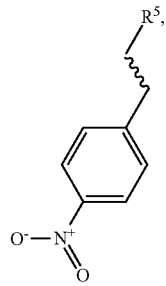
(IV)

wherein ⁓ is an alkane, alkene, or alkyne (preferably an alkene or an alkyne), and R⁵ is selected from the group consisting of formulas (V), (VI), (VII), and (VIII):

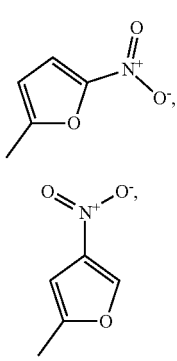
(V)

(VI)

(VII)

(VIII)

Compound (IV) comprises compound 13 and allows substitutions that do not change the activity of the protein.

Specific examples of compounds of the present invention corresponding to formula (I) are:

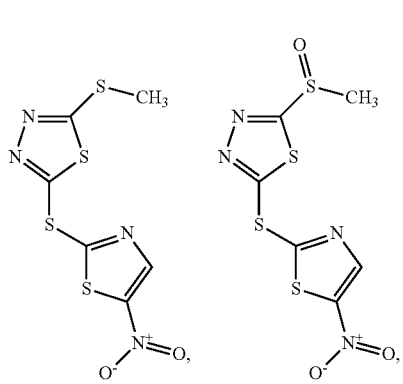

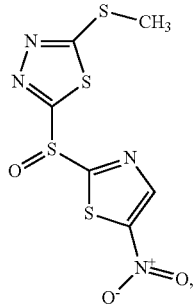

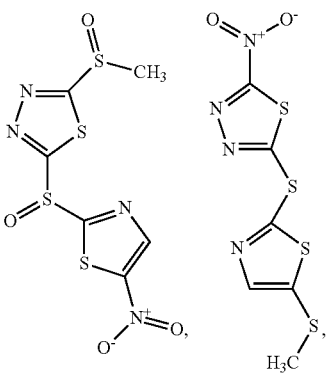

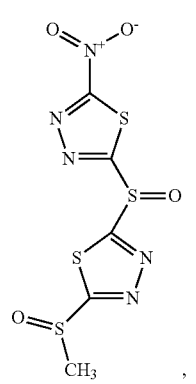

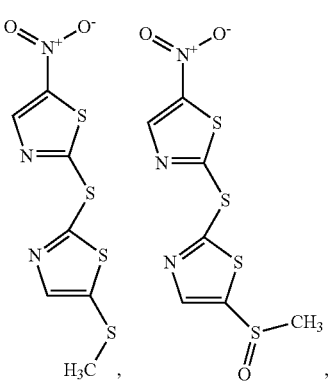

-continued
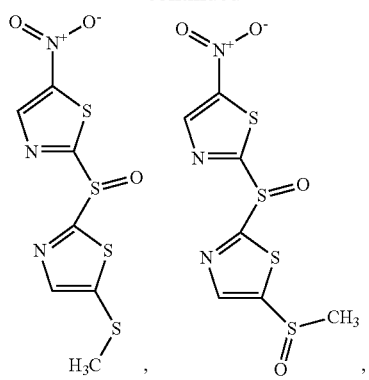
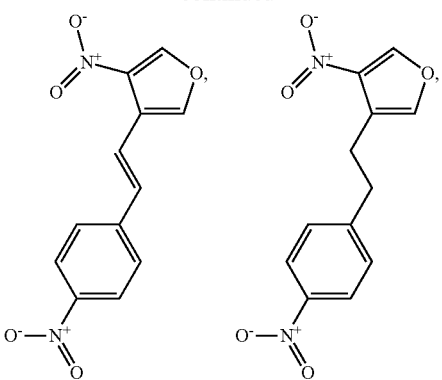
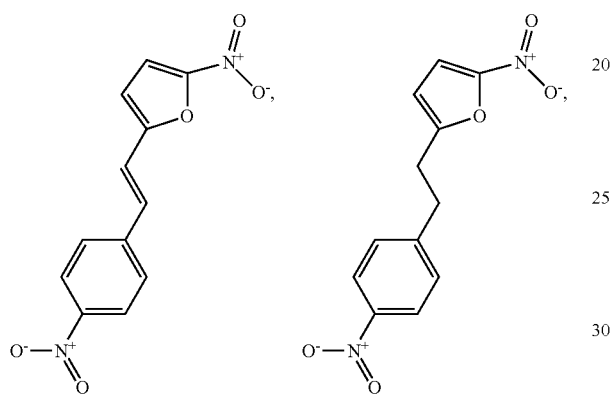
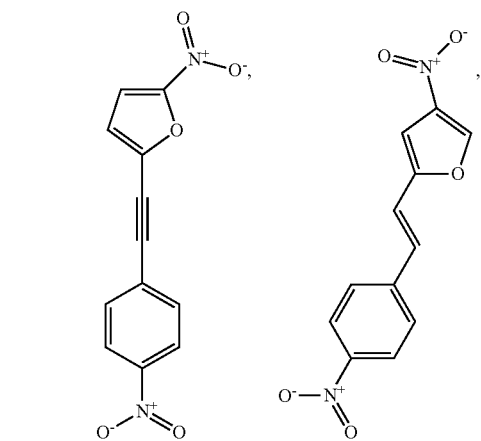
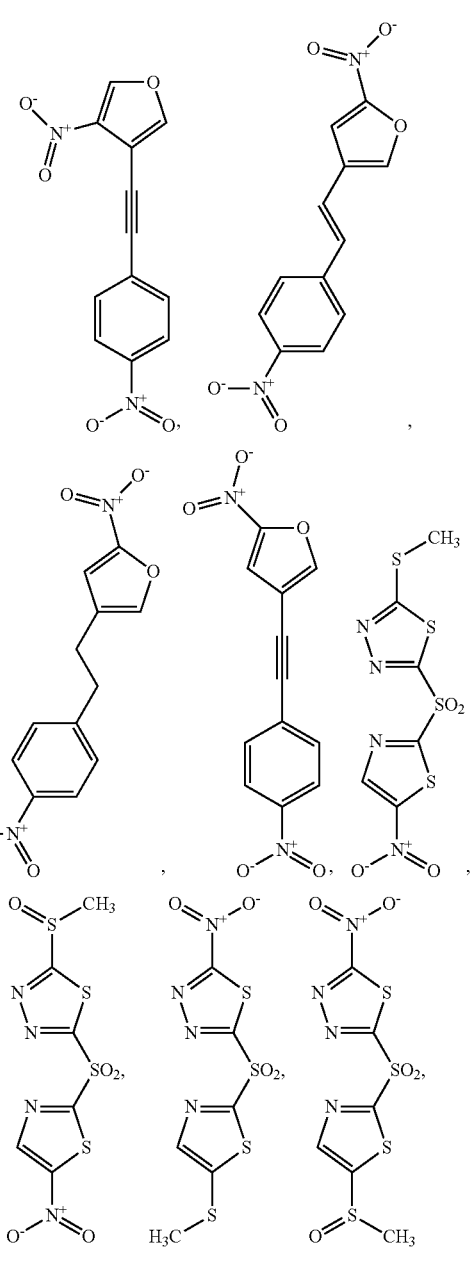
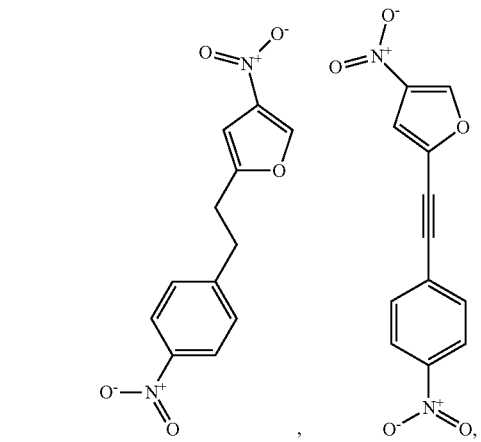

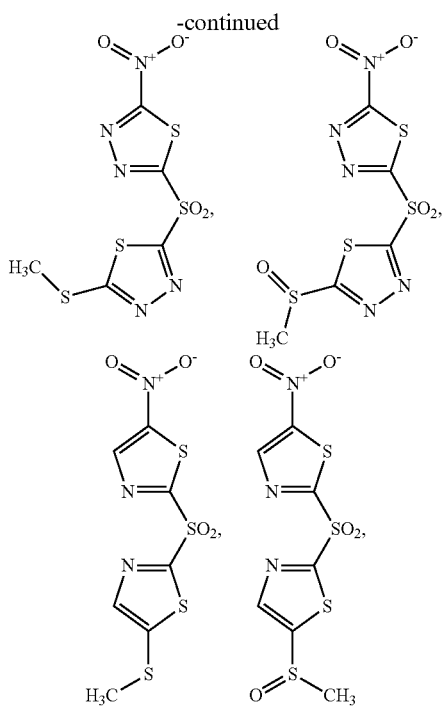

One may obtain compound 13 and compound 33 by synthesizing via methods known to one of skill in the art.

Treatments of the Present Invention

We envision that histidine kinase-dependent anti-fungal compounds of the present invention may be particularly useful in treating systemic fungal infections or deep mycoses. For example, such compounds may be used to treat bloodstream infections from *Candida* spp., pneumonia associated with *Aspergillus* spp., meningitis associated with *Cryptococcus* spp., cranial infections associated with *Rhizopus* and related spp., as well as pulmonary and disseminated infections associated with dimorphic fungi, among others.

For example, a patient suffering from a systemic fungal infection may be treated with a composition containing one or more histidine kinase-dependent anti-fungal compounds at a sufficient dosage and for a sufficient amount of time to inhibit the growth of or completely eradicate the fungal infection. Patients who may benefit from treatment with a composition containing one or more histidine kinase-dependent anti-fungal compounds include immunocompromised patients, immunosuppressed patients, patients to receive or having received solid-organ and/or hematopoietic stem cell transplants, patients to receive or having received aggressive chemotherapy, patients with AIDS, neonates, pregnant mothers, the elderly, patients infected with resistant fungal strains or multiple fungal strains, patients with advanced fungal infections, patients with early fungal infections, patients where fungal infections are suspected, patients having allergies to conventional antifungal compounds, and the like.

We further envision that the compositions of the present invention may be particularly useful in treating localized infections via topical administration or non-systemic administration, including for example, skin infections, eye infections, ear infections, infections of the nail cuticle, and the like.

We further envision that compositions containing one or more histidine kinase-dependent anti-fungal compounds may be administered prophylactically in the patients described above. This treatment is specifically important to patients preparing to undergo immunosuppressive treatments or in patients having catheters.

Formulations containing, for example, 30 milligrams (±10%) of active ingredient, or 0.1 to five hundred milligrams (±10%), or 0.1 to 200 milligrams (±10%), or 1 to 100 milligrams (±10%), or 5 to 50 milligrams (±10%) per dosage form, such as, for example, a tablet, a pill, a bolus, and the like are suitable representative unit dosage forms. Preferably, a patient may receive between 0.1 and 200 milligrams/kg (±10%) of active ingredient every 4-6 hours.

In one form of the present invention, one may wish to combine compound 13 and 33.

Duration of treatment may range from a single daily dose received for one day, to multiple doses per day for weeks or months. Duration of treatment may depend on the specific indication for therapy. For example, some fungal infections can be treated for several weeks orally or intravenously, while others may require months of treatment orally.

The invention further provides pharmaceutical formulations comprising a histidine kinase-dependent anti-fungal compound or a pharmaceutically acceptable salt or derivative thereof together with one or more pharmaceutically acceptable carriers therefore, and optionally, other therapeutic and/or prophylactic ingredients. The carrier(s) must be acceptable in the sense of being compatible with the other ingredients of the formulation and being physiologically acceptable to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

As used herein, "salts" of the instant compound may be a pharmaceutically suitable (i.e., pharmaceutically acceptable) salt including, but not limited to, acid addition salts formed by mixing a solution of the instant compound with a solution of a pharmaceutically acceptable acid. The pharmaceutically acceptable acid may be hydrochloric acid, methanesulphonic acid, fumaric acid, maleic acid, succinic acid, acetic acid, benzoic acid, oxalic acid, citric acid, tartaric acid, carbonic acid or phosphoric acid. Various pharmaceutically acceptable salts are well known in the art and may be used with the instant compound such as those previously disclosed.

For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

As used herein, "hydrates" of the instant compound may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc.

As used herein, "solvates" of the instant compound may be a pharmaceutically suitable (i.e., pharmaceutically acceptable) solvate, whereby solvation is an interaction of a solute with the solvent which leads to stabilization of the solute species in the solution, and whereby the solvated state is an ion in a solution complexed by solvent molecules. Solvates and hydrates may also be referred to as "analogues."

As used herein, "prodrugs" are compounds that are pharmacologically inert but are converted by enzyme or chemical action to an active form of the drug (i.e., an active pharmaceutical ingredient) at or near the predetermined target site. In other words, prodrugs are inactive compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction.

The phrase "hydroxy-protecting group" refers to any suitable group, such as tert-butyloxy-carbonyl (t-BOC) and t-butyl-dimethyl-silyl (TBS). Other hydroxy protecting groups contemplated are known in the art.

The pharmaceutically suitable oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, the oral dosage form includes capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), osmotic, and the like.

The oral dosage form composition contains an active pharmaceutical ingredient and may contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use.

Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

"Pharmaceutically suitable inhalation carrier systems" include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

As used herein, a transdermal dosage form includes, but is not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

The compounds of the present invention may be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier may be a finely divided solid which is in a mixture with the finely divided active component. In tablets, the active component may be mixed with the carrier having the necessary binding capacity in suitable proportions and compacted in the shape and size desired. The powders and tablets may contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component may be dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution, among others.

The compounds according to the present invention may thus be formulated for parenteral administration (for example, by injection, such as a bolus injection or continuous infusion) and may be presented in unit dose form in ampoules, pre-filled syringes, small volume infusion or in multi-dose containers with or without an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, for example, sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions may be applied directly to the nasal cavity, eye, or ear by conventional means, for example with a dropper, pipette or spray. The formulations may be provided in single or multidose form. In the latter case of a dropper or pipette, this may be achieved by the patient administering an appropriate predetermined volume of the solution or suspension. In the case of a spray, this may be achieved, for example, by means of a metering atomizing spray pump. To improve nasal delivery and retention, the compounds according to the invention may be encapsulated with cyclodextrins, or formulated with their agents expected to enhance delivery and retention in the nasal mucosa. Administration to the eye or ear may be by drops in a suitable liquid carrier, such as a saline for the eye and a viscous liquid for the ear.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

In formulations intended for administration to the respiratory tract, including intranasal formulations, the compound will generally have a small particle size, for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form.

Treatment of Medical Devices

We further envision that surfaces, preferably medical devices, including shunts, catheters, implants, intrauterine devices, subdermal capsules for extended release, and the like (collectively considered as non-limiting examples of implant dosage forms) may either be coated or impregnated with a pharmaceutical preparation containing one or more of the histidine kinase-dependent anti-fungal compounds for targeted and/or sustained release. The compounds are effective within minutes, so, in a preferred from of the method, implements would only need to be in contact the solution for a matter of minutes for sterilization. Impregnation of compound of the present invention into material used for the devices, such as catheter material, with slow release into the biofilm matrix would be another preferred means of sterilizing biofilm microbes.

Combination Treatment

We further envision that the histidine kinase-dependent anti-fungal compounds may be combined with one or more other antibiotics, including antifungals or antibacterials to provide more comprehensive therapeutic regimens. For example, histidine kinase-dependent anti-fungal compounds may be combined with one or more additional histidine kinase-dependent anti-fungal compounds and/or one or more conventional antifungal drugs. Examples of conventional antifungal drugs include: fludioxonil, polyenes, such as amphotericin B and nystatin; azoles, such as ketoconazole, fluconazole, itraconazole, voriconazole, ravuconazole, and posaconazole; antimetabolites, such as flucytosine; echinocandins, such as caspofungin, micafungin, and anidulafungin. Examples of conventional antibacterial drugs include aminoglycosides, chloramphenicol, daptomycin, fluoroquinolones, lincosamides, oxazolidinones, streptogramins, macrolides, metronidazole, mupirocin, nitrofurantoin, polypeptides, rifamycins, sulfonamides, tetracyclines, tigecycline, vancomycin, and β-lactams.

In a particularly advantageous form of the invention, the compounds of the present invention are combined with fluconazole and other azole compounds, such as voriconazole and posiconazole. An azole is a class of five-membered nitrogen heterocyclic ring compounds that contain at least one other non-carbon atom of either nitrogen, sulfur or oxygen.

Because members of the azole class are particularly effective against different fungal infections, one may wish to combine the compounds of the present invention with different azoles depending on the specific application. For example, fluconazole is particularly effective against *Candida* infections and posiconazole and voriconazole are particularly affective against Zygomycetes such as *Rhizopus* species and *Aspergillus fumigatus*, respectively.

Azoles, such as fluconazole, may be obtained from a variety of commercial sources. For example, one may obtain fluconazole and voriconazole from Sigma (for example, Sigma Aldrich, item F8929 and PZ0005).

By "combined," we mean that the azole compounds may be applied before, during or after treatment with compounds of the present invention. Most preferably, the azole compound and the compound of the present invention will be applied simultaneously.

The Examples below demonstrate the efficacy of the combination treatment. Preferably, combinations of the compounds of the present invention and fluconazole or other azole composition will be at the following dosages: fluconazole administered intravenously to adults at a dose of 800 mg×1, then, 400 mg once daily for two weeks, and to children at a dose of 3-12 mg/kg once daily (the average dose for catheter related infection would be 6 mg/kg/day given once daily for two weeks in an older child, although the dosing would be less frequent in infants less than 2 months of age.

In a particularly advantageous form of the present invention, the compounds of the present invention with members of the azole fungal inhibitor class would be used to treat either patients with fungal infections or implements, particularly medical implements, that have been infected. For example, one may wish to treat an implanted a catheter that has become compromised. One may also wish to combine compounds of the present invention with azole compounds in the agricultural methods described below.

Agricultural Methods

Agricultural/plant-based uses for histidine kinase-dependent anti-fungal compounds, either in combination with an azole compound or independently, are also contemplated. One could use the histidine kinase-dependent antifungal compounds of the present invention to treat seeds, crops, as well as lawns, trees, flowers, and the like. For example, an agricultural preparation may be a liquid composition including one or more Drk1-dependent anti-fungal compounds in addition to one or more additives, and a liquid carrier. In one embodiment, one would spray the liquid on the crops or seeds. In one embodiment, dosages would be similar to those disclosed above. An agricultural preparation may also be a particulate composition including one or more Drk1-dependent anti-fungal compounds of the present invention in addition to one or more additives. Additives may include salts, nutrients, fertilizers, preservatives, surfactants, oils, pesticides, water, pH modifiers, pH buffers, rheology modifiers, and the like.

Agricultural preparations may be administered to fields, plants, seeds, lawns, and crops to combat existing fungal infections or to prevent fungal infections. Administration may be through spraying, misting, dusting, spreading, and extended release devices, such as spikes, impregnated packaging (of seeds or crops), pellets, grains, fabrics, and the like. Administration may also be through a ground cover composition such as mulch, where the agricultural preparation may be carried by the ground cover composition to the place of treatment and may further prolong the useful duration of the ground cover composition through inhibiting decay due to fungus. Similarly, agricultural preparations may be added to building stocks, such as lumber and wood products to prolong their use.

It is further contemplated that agricultural preparations may be administered seasonally, such as before planting or seeding, after planting or seeding, or may be administered as part of processes to prepare fields such as forms of tillage.

EXAMPLES

Drk1 Homolog Analysis

Drk1 homologs were identified from fungal genomes via tBLASTn analysis using the amino acid sequence of Drk1 (GenBank Accession Number: ABF13477). As is indicated below in Table 1, Drk1 is well conserved in pathogens across the Fungal Kingdom. The homolog accession number for each homolog is listed in Table 1. The homologs were individually aligned to Drk1 using NCBI's BLAST alignment tool, and the percent identity, percent similarity, and e-value were recorded. tBLASTn analysis revealed Drk1 homologs in numerous fungal pathogens, including yeast and filamentous organisms.

TABLE 1

Histidine Kinase Homologs of Drk1.

| Organism | Accession Number | % Similarity | % Identity | E-Value |
|---|---|---|---|---|
| *Histoplasma capsulatum* | HCEG_05155.2[1] | 94 | 93 | 0 |
| *Paracoccidioides basiliensis* | PAAG_05810.1[1] | 94 | 89 | 0 |
| *Coccidioides immitis* | CIMG_04512.3 | 86 | 80 | 0 |
| *Penicillium marneffei* | ABAR01000029*,[2] | 93 | 88 | 0 |
| *Aspergillus fumigatus* | XP_754366[2] | 94 | 88 | 0 |
| *Candida albicans* | CLUG_03180.1[1] | 75 | 60 | 0 |
| *Cryptococcus neoformans* | ABD49452[2] | 54 | 42 | 0 |
| *Magnaporthe grisea* | MGG_11174.6[1] | 76 | 66 | 0 |
| *Ustilago maydis* | UM02739.1[1] | 72 | 55 | 0 |
| *Fusarium solani* | AAD09491[2] | 80 | 68 | 0 |
| *Mucor circinelloides* | Scaffold 1[3] | 68 | 54 | 0 |

[1]from the Broad Institute,
[2]from the National Center for Biotechnology Information, from the Joint Genome Institute,
*= contig.

To identify putative antifungals that act directly or indirectly through histidine kinase homologs of Drk1, we used a high throughput growth assay that uses a yeast reporter strain expressing a heterologous two-component sensor kinase (Hik1) to identify compounds that target the kinase and inhibit/kill the yeast. Hik1 and Drk1 are very closely related having near 80% amino acid sequence identity (FIG. 1). The *Saccharomyces* reporter contained an episomal plasmid with the hybrid histidine kinase Hik1 under the control of the galactose promoter (8). The *Saccharomyces* strain was provided by the Osada lab from RIKEN (Institute of Physical and Chemical Research, 2-1 Hirosawa, Wako, Saitama, 351-0198, Japan). It was used for screening initially.

The results of the Hik1 histidine kinase reporter strain were corroborated with a Drk1 reporter strain, especially regarding compounds 13 and 33. Dr. David Andes, Dr. Nancy Keller, and the clinical microbiology laboratory at the University of Wisconsin Hospital provided the microbial strains used in this study (9-12).

We screened 18,432 small molecules.

Figure 3:
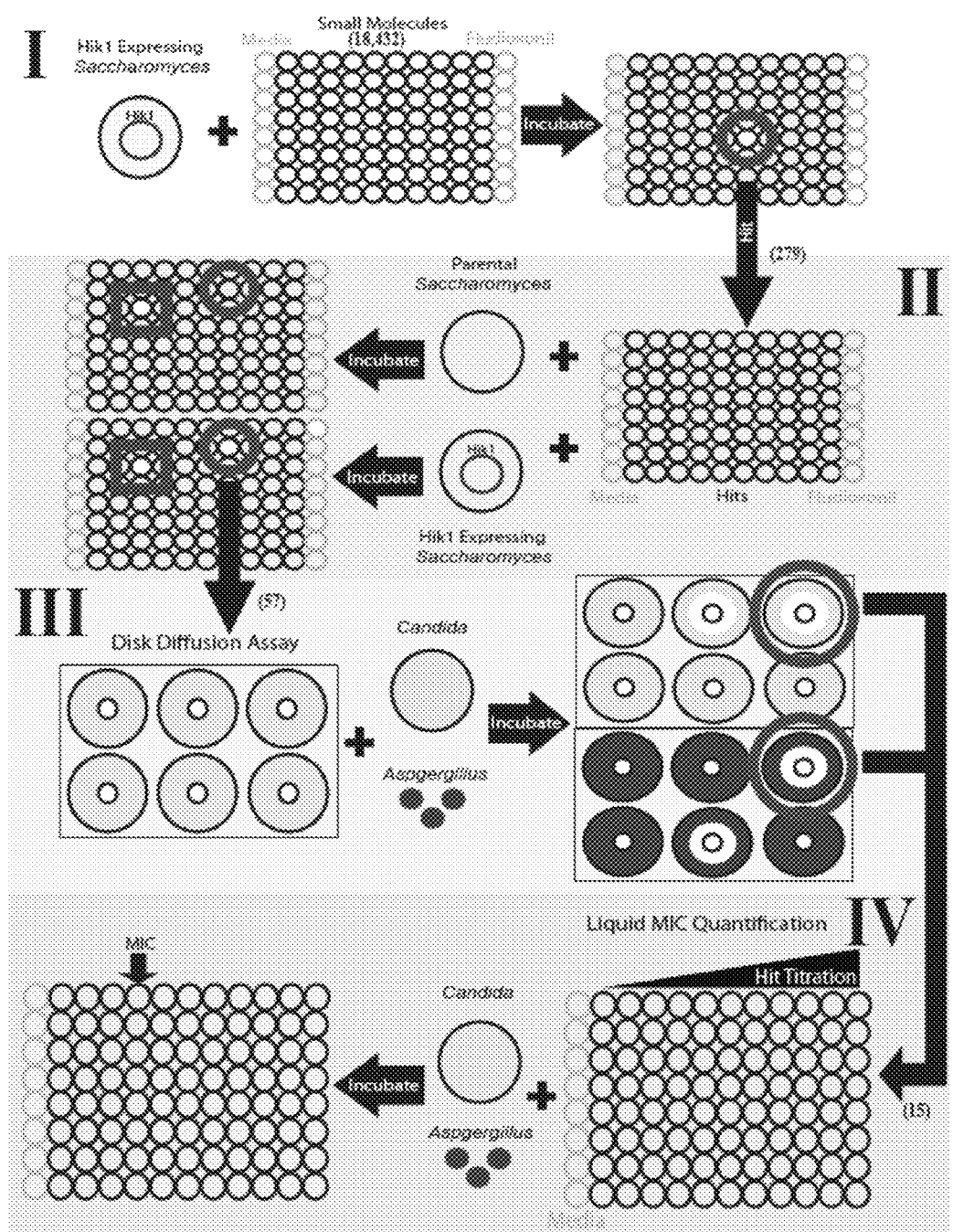
FIG. 3. Schematic of Hik1 Saccharomyces small molecule screen. The small molecule screen was performed in four stages (I-IV). Stage I—Primary screen. The Hik1 Saccharomyces was placed into 96 well plates containing small molecules. Media and fludioxonil containing wells served as negative and positive controls, respectively. Compounds that inhibited growth by at least 50% were classified as hits (circle). Stage II—Secondary screen. Hits were assayed against Hik1 and parental Saccharomyces in triplicate. Compounds that inhibited growth of both strains were discarded (squares). Compounds that only inhibited the growth of Hik1 Saccharomyces were considered to be hits (circles). Stage III—Disk diffusion. Activity against Candida and Aspergillus was initially screened via disk diffusion. Yeast or spores were suspended in top agar. Compound-containing disks were then placed on the solidified agar. Hits (gray circles) were compounds that created zones of inhibition (white circles) against both organisms. Stage IV—Microbroth dilution. The Minimum Inhibitory Concentration (MIC) of each drug was quantified through microbroth dilution. Compounds were serially diluted in 96 well plates, Candida or Aspergillus was added, and the plates were incubated. The MIC was defined as the lowest compound concentration that prevented growth.

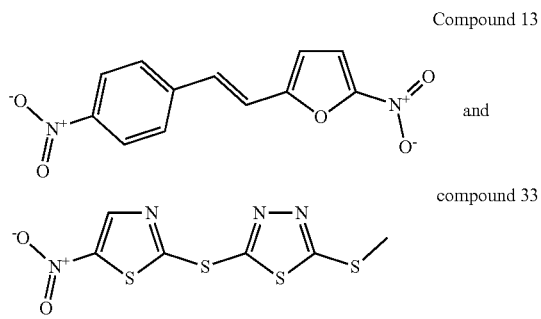

were found to specifically inhibit the growth of the reporter strain. An overview of the screening process is illustrated in FIG. 3. The small molecules assayed in the screen were obtained from the Maybridge HITFINDER® collection (ThermoFisher Scientific, Waltham, Mass.). The compounds tested have greater than 90% purity and were stored in 100% DMSO at a concentration of 1 mM.

Small Molecule Screening

The small molecule screen was performed in four stages.

Stage I—Preliminary Screen:

An overnight culture of the Hik1 *Saccharomyces* strain, grown in SC minimal raffinose media—0.67% yeast nitrogen base without amino acids with ammonium sulfate (Difco, BD, Franklin Lakes, N.J.), 2% raffinose (Sigma, St. Louis, Mo.), 0.01% adenine, arginine, cysteine, leucine, lysine, threonine, and tryptophan (Sigma), and 0.005% aspartic acid, histidine, isoleucine, methionine, phenylalanine, proline, serine, tyrosine, and valine (Sigma), was diluted to an $OD_{600\ nm}$ of 0.2 in SC minimal galactose media—0.67% yeast nitrogen base without amino acids with ammonium sulfate (Difco), 2% raffinose (Sigma), 0.01% adenine, arginine, cysteine, leucine, lysine, threonine, and tryptophan (Sigma), and 0.005% aspartic acid, histidine, isoleucine, methionine, phenylalanine, proline, serine, tyrosine, and valine (Sigma). A 100 μl aliquot of galactose medium was added to each well of a 96 well plate. Candidate small molecule compounds were then added to the plate at a final concentration of 10 μM. A 100 μl aliquot of *Saccharomyces* yeast reporter was then added to each well, resulting in a final yeast concentration of 0.1 $OD_{600\ nm}$. Aliquots of 100 μl of yeast were also added to medium-only and medium+fludioxonil wells, which served as negative and positive controls, respectfully. The plates were incubated at 30° C. overnight. Growth was quantified by absorbance at $600_{nm}$ using an automated plate reader. A compound was considered a hit if it caused at least a 50% reduction in growth compared to the positive controls.

Stage II—Secondary Screen:

Hit compounds were subjected to a secondary screen. Compounds were tested against reporter and parental *Saccharomyces* strains in triplicate. Medium-only and medium+fludioxonil wells again served as positive and negative controls, respectively. Hit compounds that reduced the growth of the reporter strain at least 50% but did not cause a reduction in growth of the parental strain were classified as hits and selected for further testing.

Stage III—Disk Diffusion:

Small molecule activity against the fungal pathogens *Candida albicans* and *Aspergillus fumigatus* was evaluated using an agar disk diffusion assay. Yeast ($1 \times 10^4$) from an overnight culture of *C. albicans* was suspended in 600 μl of top agar (1% yeast extract (ThermoFisher), 2% peptone (ThermoFisher), 2% dextrose (Sigma), and 0.5% agar (Fisher)). This suspension was spread and allowed to solidify on 5 ml of base agar (YPD media containing 2% agar) in the well of a 6-well plate. Disks (6 mm AA, Whatman Inc., Piscataway, N.J., Cat#2017-006) were aseptically placed on a sterile Petri dish lid. Compounds selected from stage II (1 μg total) were each suspended in 100% dimethyl sulfoxide (DMSO) to a total volume of 5 μl, added to separate disks, and allowed to dry for five minutes. Fludioxonil (Sigma) and DMSO-only disks served as positive and negative controls, respectively. Disks were placed into separate wells and incubated at room temperature for 48 hours. Antifungal activity was determined based on the size of the zone of inhibition of *C. albicans* growth.

Figure 4:
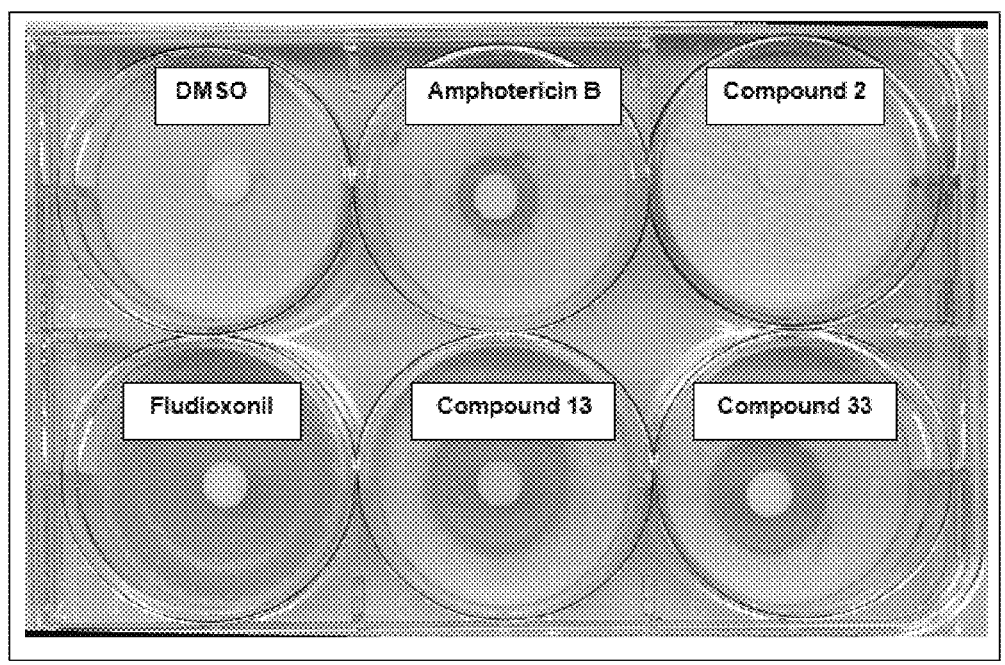
FIG. 4. Disk diffusion demonstrated the robust activity of Compounds 13 and 33 against Aspergillus fumigatus. Disks containing 1 μg of test compound were placed on top of agar containing A. fumigatus spores. The negative control, dimethyl sulfoxide (DMSO) had no effect on Aspergillus growth, but fludioxonil and amphotericin B, which served as positive controls, created zones of inhibition. Small molecules, like compound 2, did not inhibit fungal growth and were discarded. Compounds 13 and 33 inhibited growth and were the focus of further study.
Figure 5A:
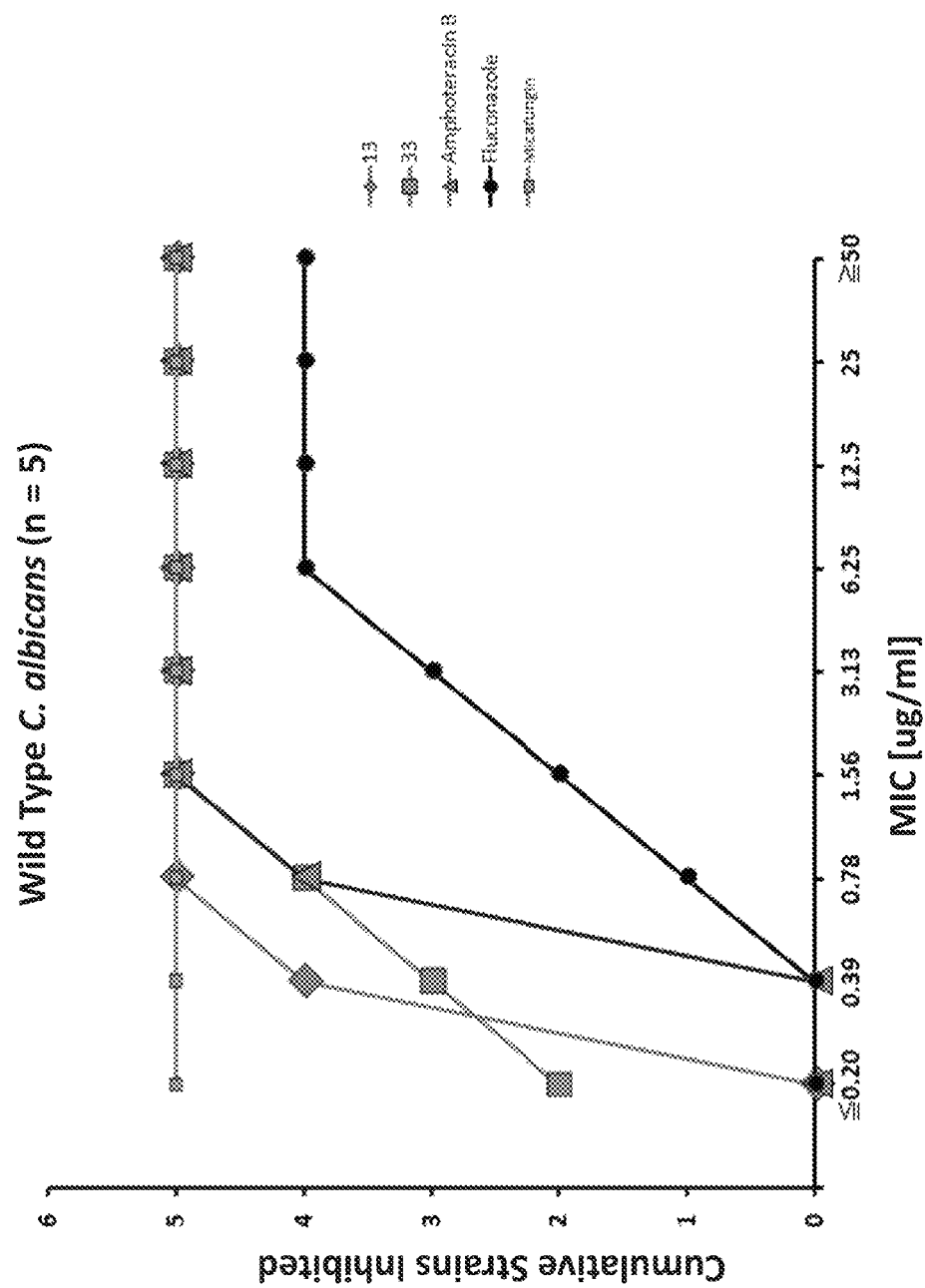
FIG. 5A. Similar cumulative inhibition of fungal pathogens by compounds 13 and 33 compared to commercial antifungals. Microbroth dilution enabled the quantification of compound Minimum Inhibitory Concentrations (MICs) against numerous fungal pathogens. Compounds 13 and 33 were active against Candida albicans.
Figure 5B:
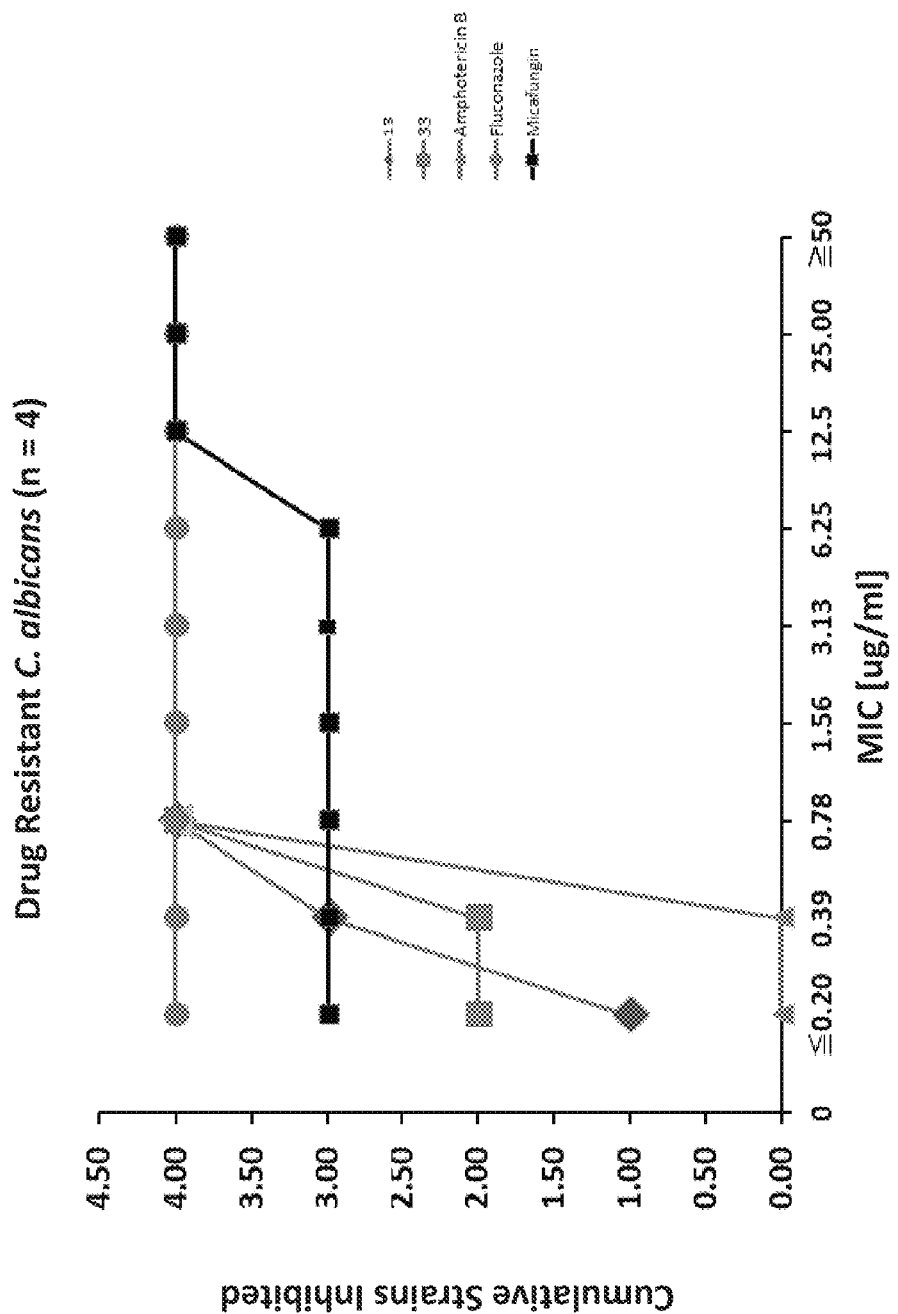
FIG. 5B. Similar cumulative inhibition of fungal pathogens by compounds 13 and 33 compared to commercial antifungals. Compounds 13 and 33 were active against C. albicans resistant to conventional antifungals fluconazole and micafungin.
Figure 5C:
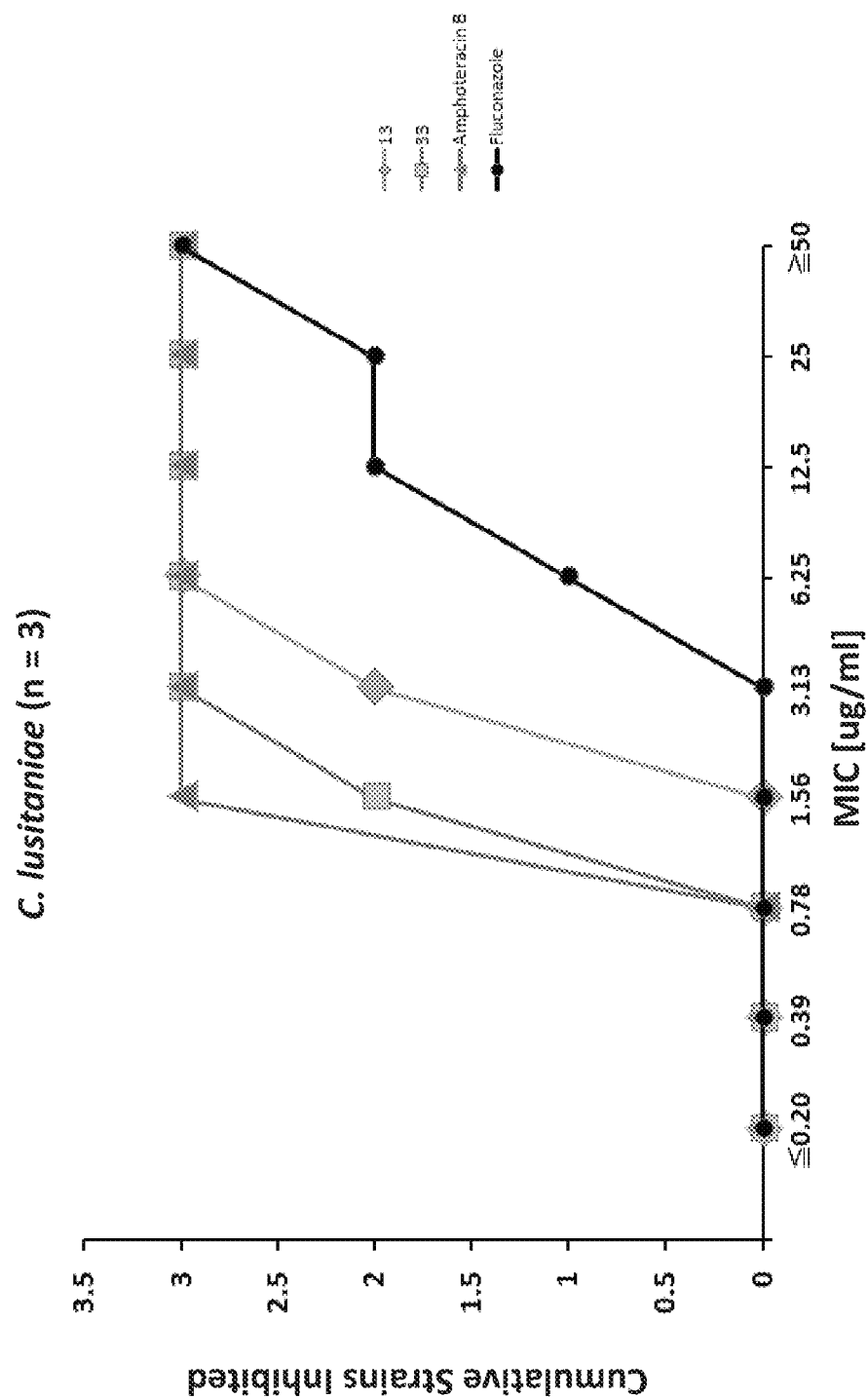
FIG. 5C. Similar cumulative inhibition of fungal pathogens by compounds 13 and 33 compared to commercial antifungals. Compounds 13 and 33 were active against C. lusitaniae.
Figure 5D:
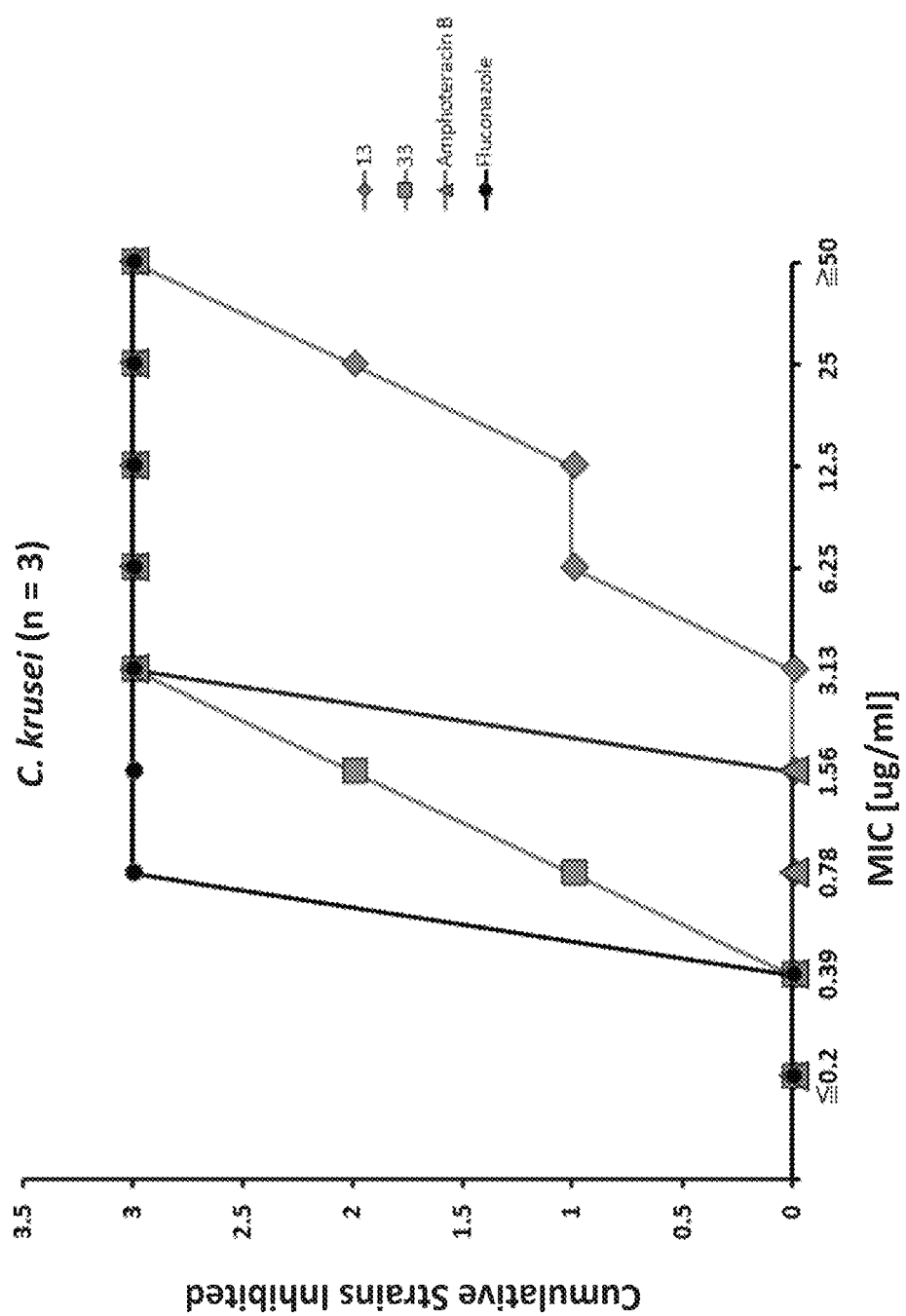
FIG. 5D. Similar cumulative inhibition of fungal pathogens by compounds 13 and 33 compared to commercial antifungals. Compounds 13 and 33 were active against C. krusei.
Figure 5E:
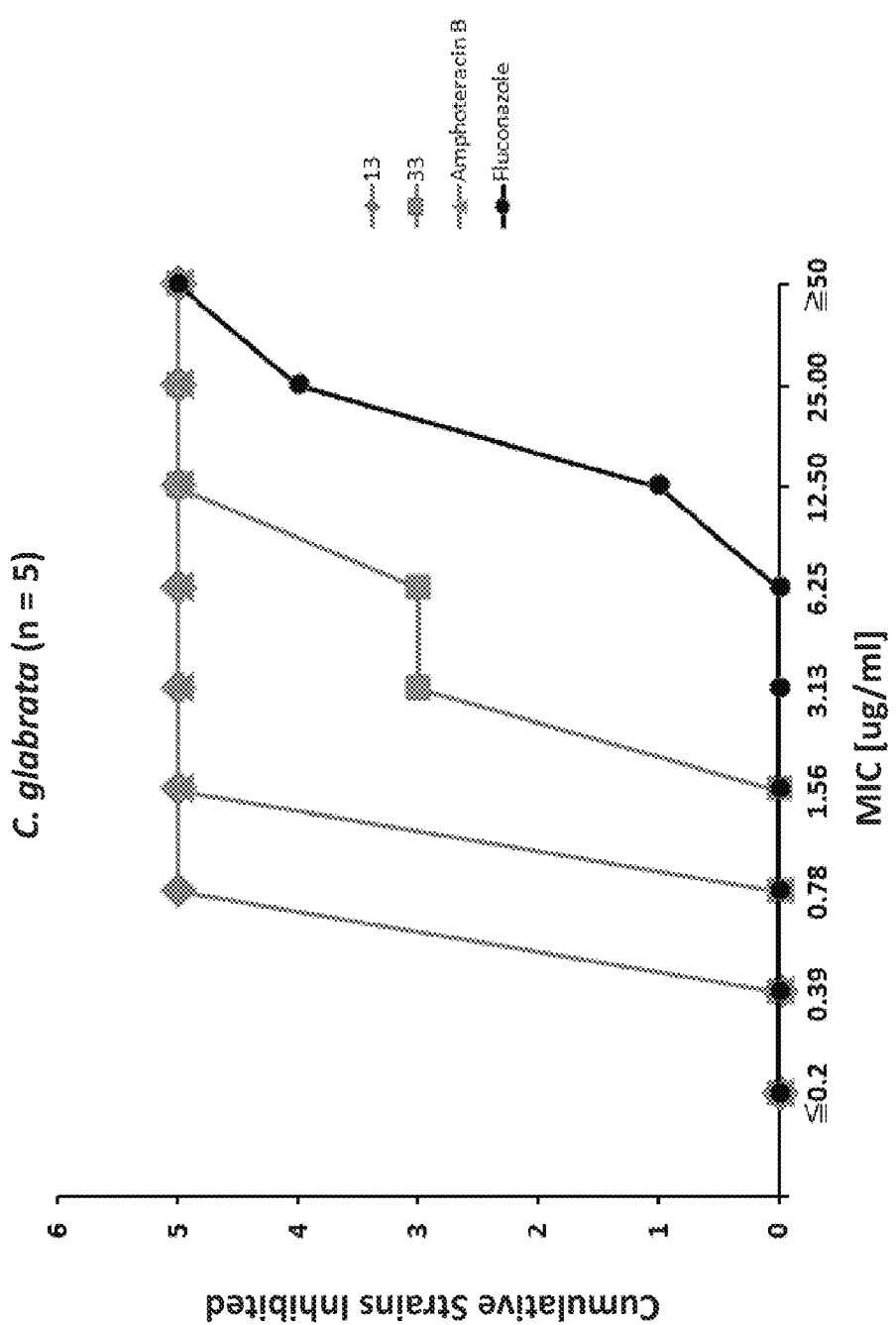
FIG. 5E. Similar cumulative inhibition of fungal pathogens by compounds 13 and 33 compared to commercial antifungals. Compounds 13 and 33 were active against C. glabrata.
Figure 5F:
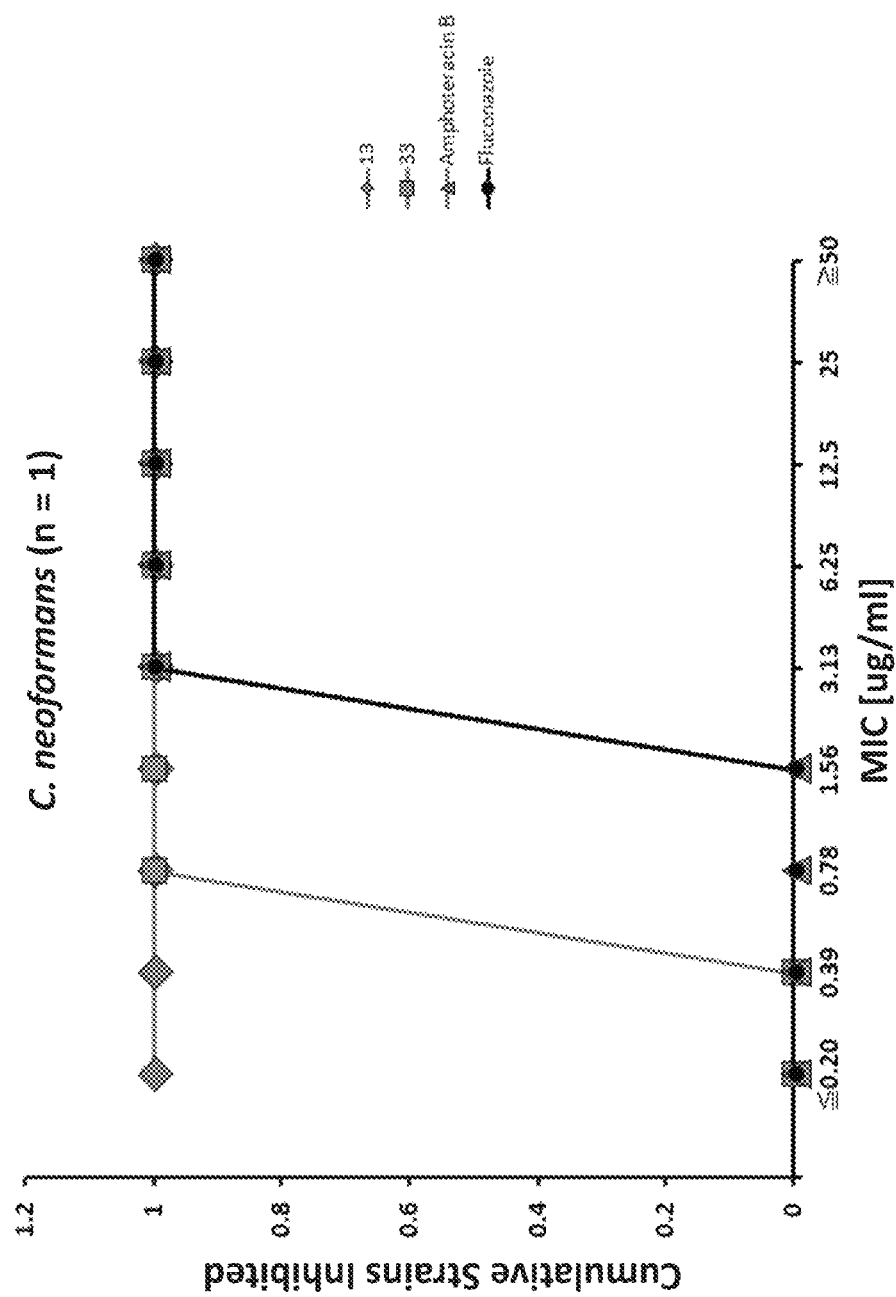
FIG. 5F. Similar cumulative inhibition of fungal pathogens by compounds 13 and 33 compared to commercial antifungals. Compounds 13 and 33 were active against Cryptococcus neoformans.
Figure 5G:
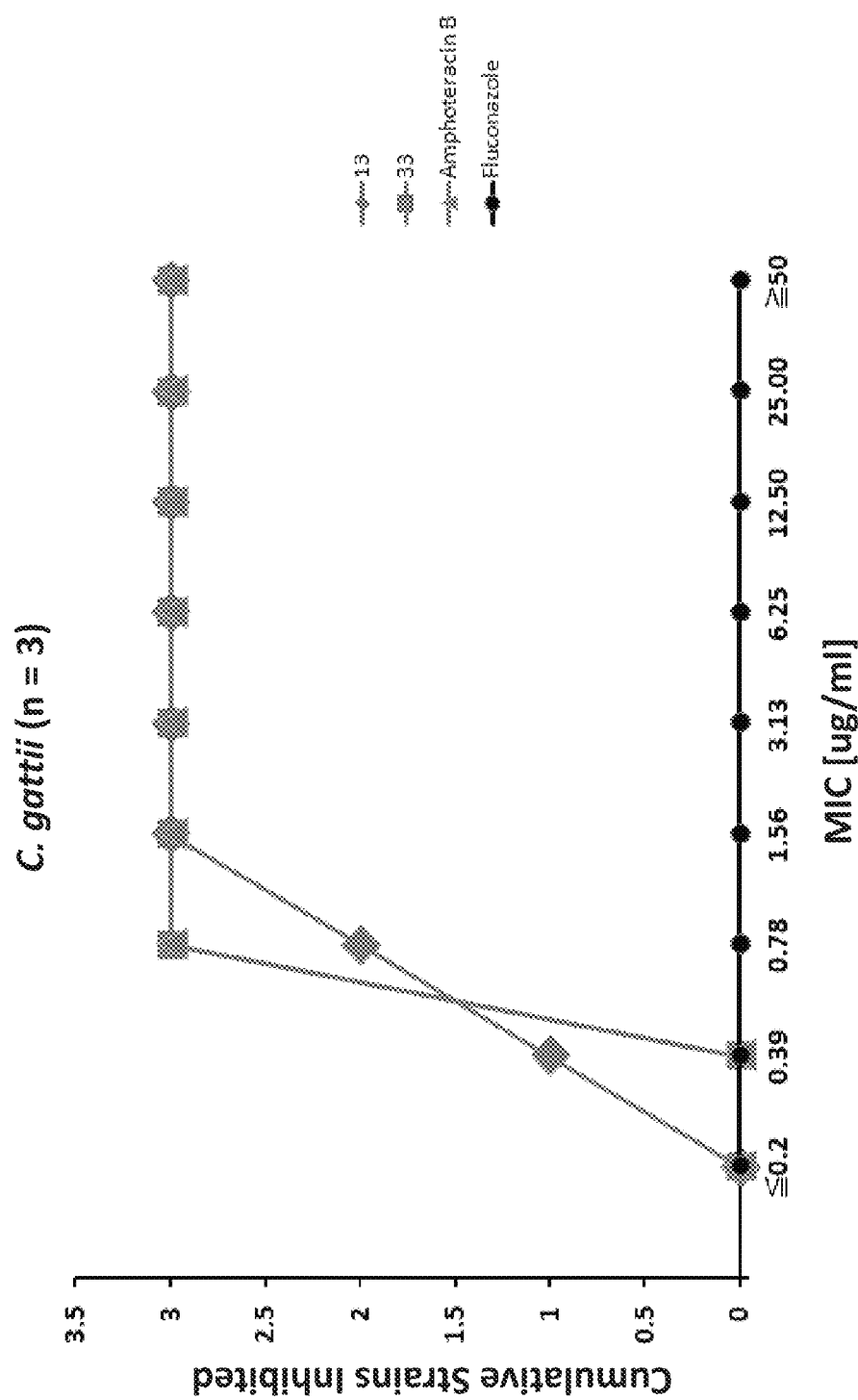
FIG. 5G. Similar cumulative inhibition of fungal pathogens by compounds 13 and 33 compared to commercial antifungals. Compounds 13 and 33 were active against C. gattii.
Figure 5H:
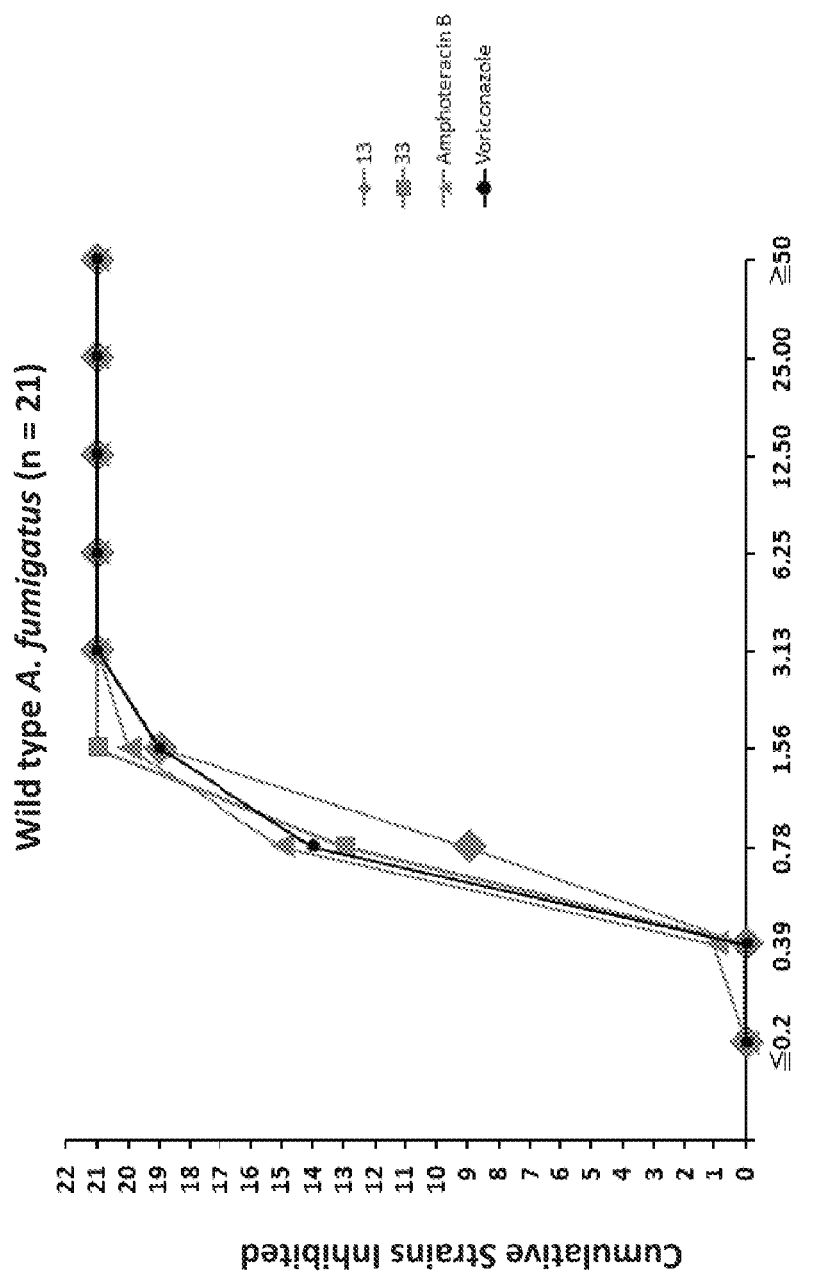
FIG. 5H. Similar cumulative inhibition of fungal pathogens by compounds 13 and 33 compared to commercial antifungals. Compounds 13 and 33 were active against wild type *Aspergillus fumigatus*.
Figure 5I:
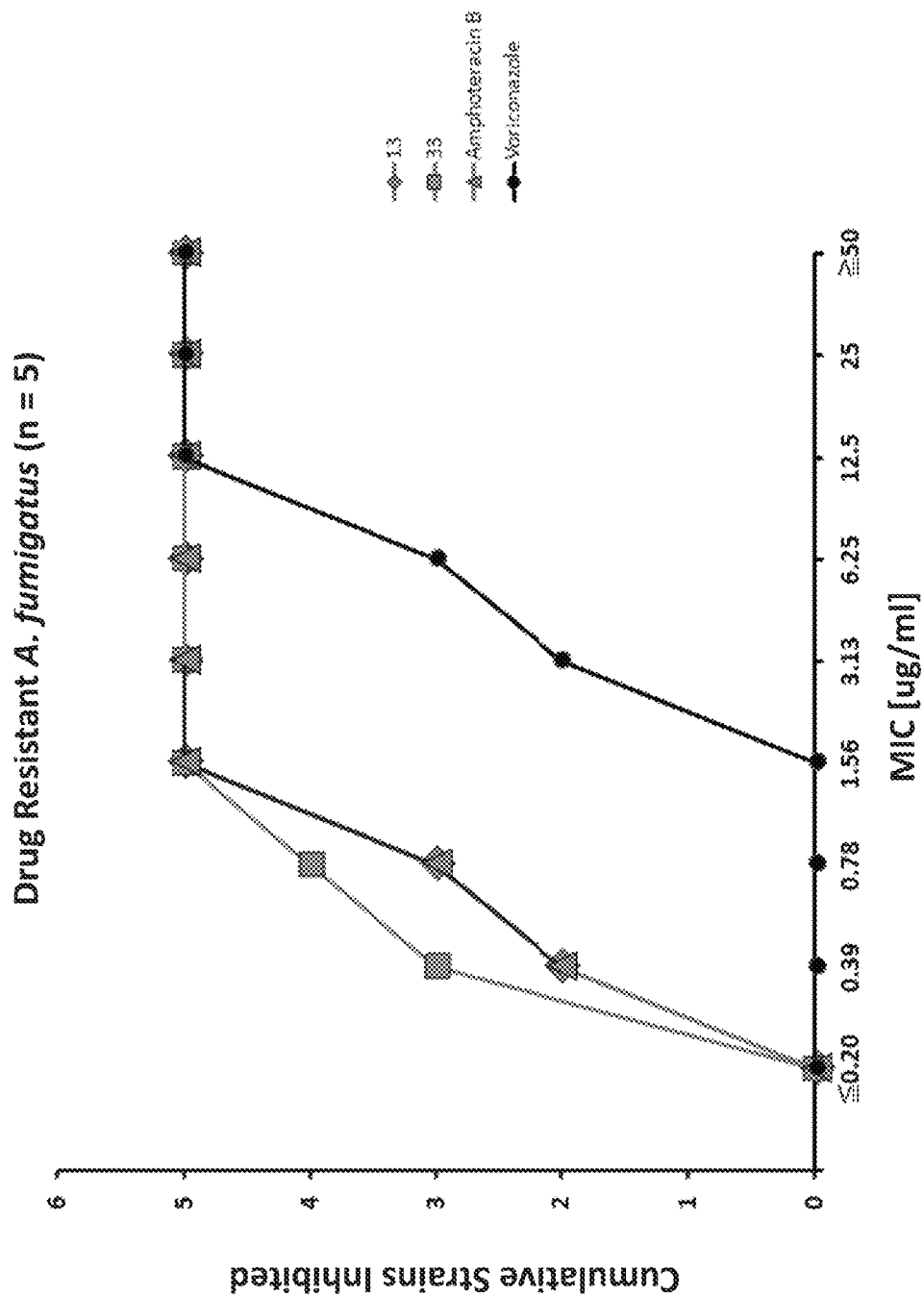
FIG. 5I. Similar cumulative inhibition of fungal pathogens by compounds 13 and 33 compared to commercial antifungals. Compounds 13 and 33 were active against drug resistant *A. fumigatus*.
Figure 6:
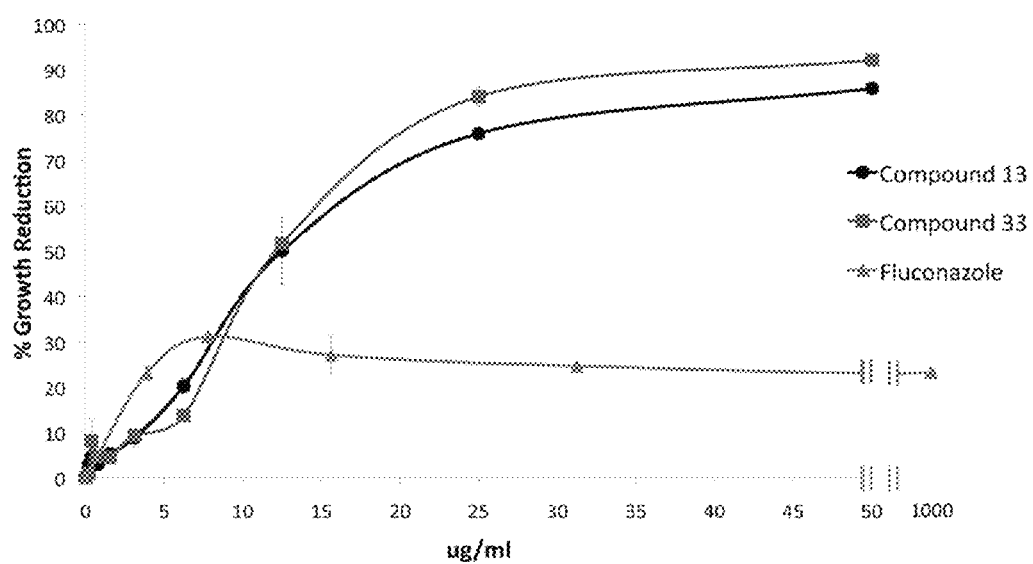
FIG. 6. Activity of compounds 13 and 33 against *Candida albicans* biofilms. Fluconazole was ineffective against *Candida* biofilms at concentrations up to 1000 μg/ml. Compounds 13 and 33 significantly inhibited *Candida* biofilm growth at concentrations as low as 25 μg/ml. The experiment was performed in triplicate. Error bars represent the standard deviation. These data are representative of two independent experiments.

Activity against *A. fumigatus* was determined following the aforementioned disk diffusion assay. The protocol only differed in that $6.0 \times 10^5$ conidia were used instead of yeast, and the plates were incubated at 37° C. for 48 hours instead of room temperature (FIG. 4).

Stage IV—Microbroth Dilution:

Clinical and Laboratory Standards Institute (CLSI) protocol M27 was used to quantify the minimum inhibitory concentration (MIC) of compounds 13 and 33 against yeast fungal pathogens (13). Briefly, compounds were solubilized in 100% DMSO and serially diluted two-fold in a 96 well plate in 100 μl of RPMI medium. A 100 μl aliquot of RPMI medium containing $3 \times 10^3$ yeast/ml of an overnight culture was then added to each well. Medium, medium+yeast, and medium+yeast+DMSO wells were prepared as controls. Each well was prepared in triplicate. The plates were incubated at 35° C. for 48 hours. The MIC concentration was defined as the concentration at which no growth was visible by eye and the results verified by plating on YPD agar. The experiment was performed in duplicate. MIC concentrations were also defined against filamentous fungi using the CLSI protocol M38 (14). This protocol only differed from M27 in that 100 μl of medium containing $4 \times 10^5$ spores/ml were added instead of yeast (FIG. 5A-I).

*Candida* Biofilm Experiments

Compound activity against *C. albicans* biofilm was assessed using a 96-well plate format as previously described by Nett et al. (15). Briefly, the *C. albicans* inoculum was prepared by diluting an overnight culture grown at 37° C. in RPMI-MOPS to $1 \times 10^6$ in RPMI-MOPS based on hemocytometer counts. An aliquot of 100 μl of the inoculum was added to each well of a 96-well flat-bottom polystyrene plate. After a 6-h incubation at 37° C., the wells were washed with phosphate-buffered saline (PBS) three times to remove any non-adherent cells. Fresh medium and fluconazole (Sigma), compound 13, and compound 33 were added and the plates were incubated at 37° C. for 24 hours. The XTT reduction assay was used to quantify the viability of biofilm cell as previously described (11). Briefly, 90 μl of (2,3)-bis-(2-Methoxy-4-Nitro-5-Sulphenyl)-(2H)-Tetrazolium-5-Carboxanilide (XTT; 1 mg/ml) (Sigma) and 10 μl phenazine methosulfate (320 μg/ml) (Sigma) were added to each well, and the plate was incubated for 2 h at 37° C. Cell viability was determined by measuring the absorbance at 490 nm using an automated plate reader. The biofilm growth assay was performed in duplicate.

Hemolytic Assay

Figure 7:
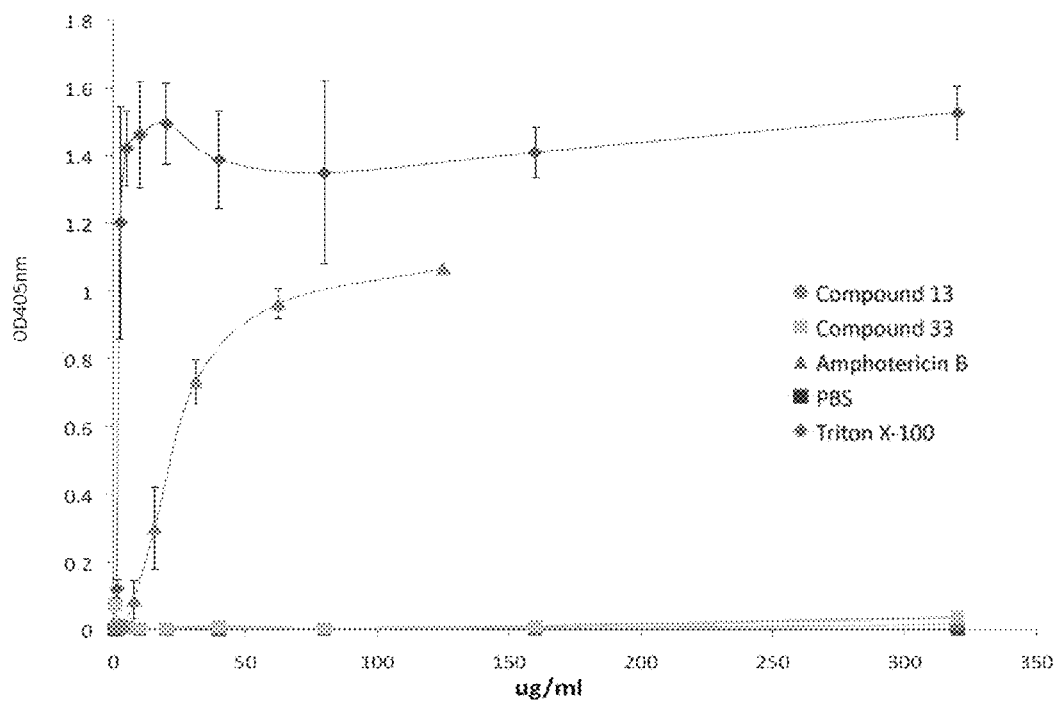
FIG. 7. Compounds 13 and 33 are less hemolytic that amphotericin B. Heme release was quantified by measuring the absorbance at 405 nm. Triton X-100 and phosphate buffered saline served as positive and negative controls for hemolysis, respectively. The experiment was performed in triplicate. Error bars represent the standard deviation.

A hemolytic assay was used to compare relative drug toxicity among compounds 13 and 33 and amphotericin B, as previously described by Raguse et al. (16). Briefly, human red blood cells (RBCs) were isolated via FICOLL® (Sigma) gradient centrifugation and stored on ice. The RBCs were pelleted by centrifugation and washed with PBS a total of three times. A 2% RBC suspension in PBS was made and stored on ice for less than one hour. Drugs were suspended in DMSO and two-fold serial dilutions were prepared in PBS with a total volume of 100 µl in a 96-well round-bottom plate in triplicate. Wells containing PBS and Triton X-100 (Sigma) were used as negative and positive controls of hemolysis, respectively. A 100 µl aliquot of the 2% RBC suspension was then added to each well. The plate was then incubated at 37° C. for one hour. The plate was then centrifuged at 2,500 rpm for five minutes to pellet the RBCs. A 50 µl aliquot of the supernatant was transferred to a fresh 96-well plate, and absorbance at 405 nm was measured using an automated plate reader to quantify heme release. The experiment was performed in triplicate (FIG. 7).

Investigation of Inhibition of Plant Fungal Pathogen

Figure 8:
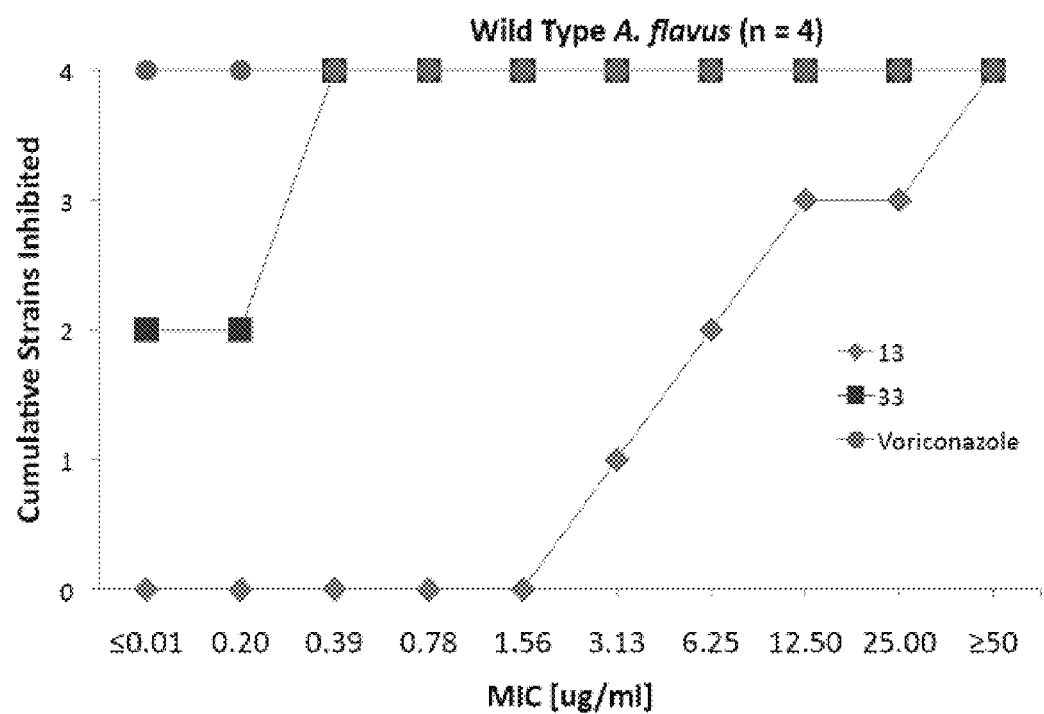
FIG. 8. Cumulative inhibition of the plant fungal pathogen, *Aspergillus flavus*, by compounds 13 and 33. Microbroth dilution enabled the quantification of compound MICs against four isolates of *A. flavus*.

To determine whether compounds 13 and 33 would be effective against plant fungal pathogens, a microbroth dilution assay, as described above, was performed using 4 different isolates of the plant fungal pathogen, *Aspergillus flavus* (11). Briefly, the MICs of compounds 13 and 33 were determined for each of the 4 isolates and compared with the conventional antifungal compound, voriconazole (available from Sigma). The experiment was performed in quadruplicate (FIG. 8).

In Vitro Biofilm Drug Synergy

*Candida* biofilms were formed in 96-well flat-bottom polystyrene plates (Fischer) as described previously (Nett J E, Cain M T, Crawford K, Andes D R. Optimizing a *Candida* Biofilm Microtiter Plate Model for Measurement of Antifungal Susceptibility by XTT Assay. J. Clin. Microbiol. 2011 Jan., 2). Cells from an overnight culture grown in YPD shaking at 37° C. were enumerated by hemocytometer and suspended in RPMI-MOPS (Fisher) at a concentration of $10^6$ cells/ml. A 100 µl of inoculum was added to each well of the plate.

After 6 h incubation at 37° C., biofilms were gently washed twice with phosphate-buffered saline (PBS) to remove unattached cells. Dilutions of fluconazole (62.5 to 1,000 µg/ml) (Fisher), Compound 13 (0.1 to 25 µg/ml), and Compound 33 (0.1 to 25 µg/ml) were examined alone and in combination in a checkerboard format. The ranges of concentrations of the fluconazole used included the standard doses given to humans. After overnight incubation at 37° C., biofilms were washed twice with PBS.

Measurement of biofilm cell metabolic activity using the XTT reduction assay was performed as previously described (Nett J E, Cain M T, Crawford K, Andes D R. Optimizing a *Candida* Biofilm Microtiter Plate Model for Measurement of Antifungal Susceptibility by XTT Assay. J. Clin. Microbiol. 2011 January, Uppuluri P, Nett J, Heitman J, and Andes D. Synergistic Effect of Calcineurin Inhibitors and Fluconazole against *Candida albicans* Biofilms. Antimicrob Agents Chemother. 2008 March; 52(3): 1127-1132). Briefly, 90 µl of XTT at 1 mg/ml (Sigma) and 10 µl phenazine methosulfate at 320 µg/ml (Sigma) were added to each well, and the plate was incubated at 37° C. for 2 h. Viable cell number was assessed using the Absorbance at $492_{nm}$ measured using an automated plate reader. Assays were performed in duplicate. The drug concentration resulting in a 25% reduction in optical density compared to the no-drug control wells was determined ($EC_{25}$).

Synergy was determined using the fractional inhibitory concentration (FIC). FIC was calculated using effective concentration (EC) as follows: [($EC_{25}$ of drug A in combination)/($EC_{25}$ of drug A alone)]+[($EC_{25}$ of drug B in combination)/($EC_{25}$ of drug B alone)]. Values of ≤0.5 revealed synergy as described (Uppuluri P, Nett J, Heitman J, and Andes D. Synergistic Effect of Calcineurin Inhibitors and Fluconazole against *Candida albicans* Biofilms. Antimicrob Agents Chemother. 2008 March; 52(3): 1127-1132).

Figure 9B:
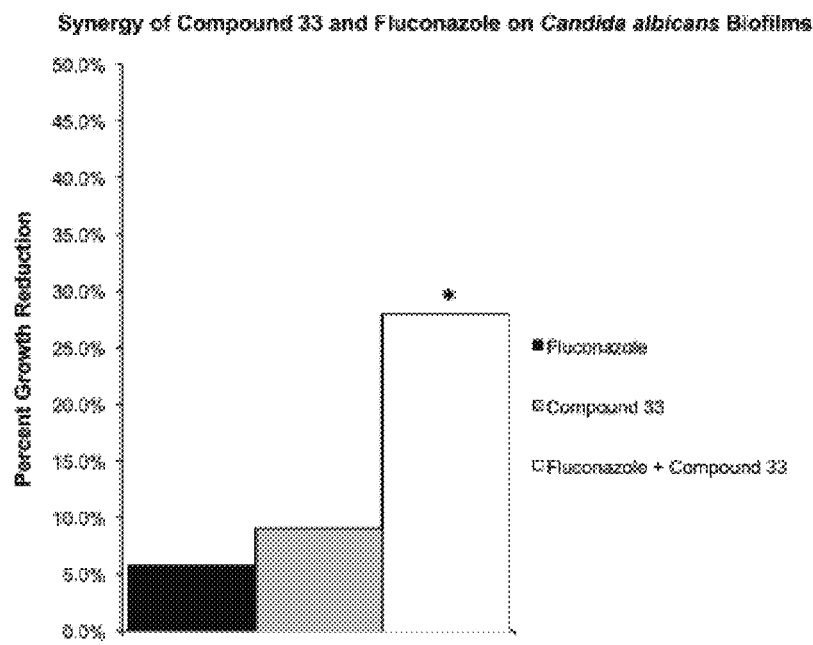
FIG. 9B. Compounds 13 and 33 have synergy with Fluconazole against *Candida albicans* biofilm. *Candida albicans* biofilm was exposed to compound 33 and Fluconazole alone and in combination. Synergy was determined using fractional inhibitory concentration (FIC). Values ≤0.5 indicate synergy (*).
Figure 9A:
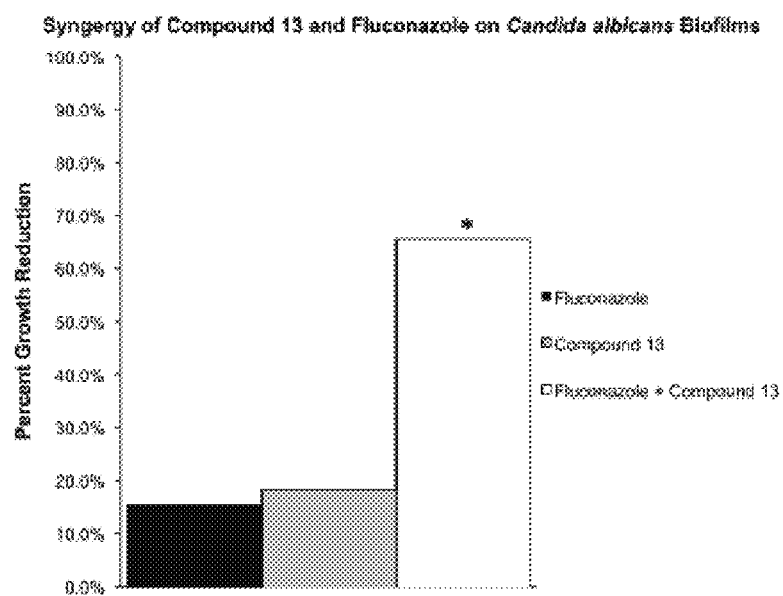
FIG. 9A. Compounds 13 and 33 have synergy with Fluconazole against *Candida albicans* biofilm. *Candida albicans* biofilm was exposed to compound 13 and Fluconazole alone and in combination. Synergy was determined using fractional inhibitory concentration (FIC). Values ≤0.5 indicate synergy (*).

FIG. 9 demonstrates synergy of both compound 33 and compound 13 in combination with fluconazole. Note that compound 33 in combination with fluconazole demonstrated an approximately 28% growth reduction, in comparison with approximately 6% growth reduction with fluconazole by itself and approximately 9% growth reduction with compound 33 by itself. Similarly, a combination of fluconazole and compound 13 resulted in approximately 65% growth reduction, compared with 15% growth reduction with fluconazole and 18% growth reduction with compound 13.

Combinations of fluconazole at 62.5 ug/ml, 13 at 0.8 ug/ml, and 33 at 1.6 ug/ml resulted in the bar graph of FIG. 9. Fluconazole concentration used to generate the data for FIG. 9 is within the daily dose recommended for fluconazole. Fluconazole is typically administered intravenously to adults at a dose of 800 mg×1, then 400 mg once daily for two weeks, and to children at a dose of 3-12 mg/kg once daily (the average dose for catheter related infection would be 6 mg/kg/day given once daily for two weeks in an older child, although the dosing would be less frequent in infants less than 2 months of age.

We claim:

1. A method for treating fungal infection, comprising:
   (a) identifying a plant or animal having a fungal infection; and
   (b) administering an effective amount of an anti-fungal compound to the plant or animal, wherein the amount is effective to reduce the fungal infection and wherein the compound is represented by formula (IV),

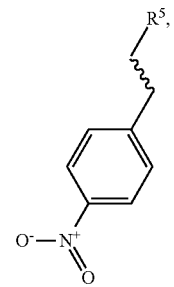

(IV)

wherein ～～ is an alkane, alkene, or alkyne, and $R^5$ is selected from the group consisting of formulas (V), (VI), (VII), and (VIII):

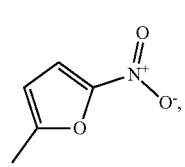

(V)

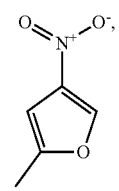

(VI)

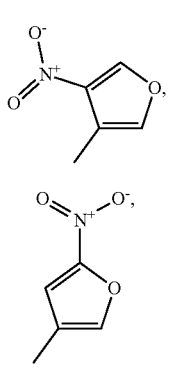
(VII)

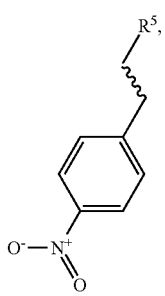
(VIII)

or a salt, solvate or hydrate thereof.

2. The method of claim 1 wherein the histidine kinase-dependent anti-fungal compound is:

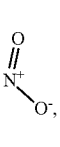

or a salt, solvate or hydrate thereof.

3. The method of claim 1 additionally comprising administering an amount of an azole compound effective to reduce fungal infection.

4. The method of claim 3 wherein the azole is fluconazole.

5. The method of claim 1, wherein the compound is a histidine kinase-dependent antifungal compound.

6. The method of claim 5, wherein the histidine kinase is Drk1.

7. A method for preventing a fungal infection, comprising: administering an effective amount of a composition comprising a compound of formula (IV) to a plant or animal, wherein the amount is effective to prevent a fungal infection,

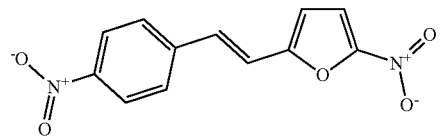
(IV)

wherein ∼∼∼ is an alkane, alkene, or alkyne, and $R^5$ is selected from the group consisting of formulas (V), (VI), (VII), and (VIII):

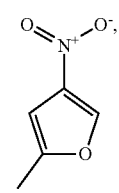
(V)

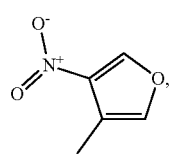
(VI)

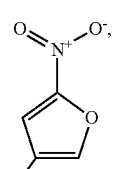
(VII)

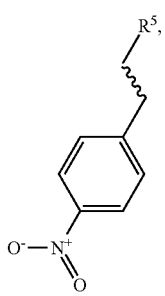
(VIII)

or a salt, solvate or hydrate thereof.

8. The method of claim 7 wherein the compound is:

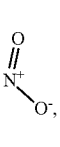

or a salt, solvate or hydrate thereof.

9. The method of claim 7 additionally comprising administering an amount of an azole compound effective to reduce fungal infection.

10. The method of claim 7 wherein the azole is fluconazole.

* * * * *